United States Patent
Carroll et al.

(10) Patent No.: US 9,078,401 B2
(45) Date of Patent: Jul. 14, 2015

(54) METHODS FOR VEGETATIVE PROPAGATION OF GRASS PLANTS

(75) Inventors: John Todd Carroll, Snohomish, WA (US); Norman Volotin, Seattle, WA (US)

(73) Assignee: TreeFree Biomass Solutions, Inc., Seattle, WA (US)

( * ) Notice: Subject to any disclaimer, the term of this patent is extended or adjusted under 35 U.S.C. 154(b) by 153 days.

(21) Appl. No.: 13/389,669

(22) PCT Filed: Aug. 13, 2010

(86) PCT No.: PCT/US2010/045424
§ 371 (c)(1),
(2), (4) Date: Apr. 20, 2012

(87) PCT Pub. No.: WO2011/019984
PCT Pub. Date: Feb. 17, 2011

(65) Prior Publication Data
US 2012/0204487 A1    Aug. 16, 2012

Related U.S. Application Data

(60) Provisional application No. 61/233,713, filed on Aug. 13, 2009.

(51) Int. Cl.
| | | |
|---|---|---|
| *C12N 5/00* | (2006.01) | |
| *C12N 5/02* | (2006.01) | |
| *A01G 1/00* | (2006.01) | |
| *A01G 7/06* | (2006.01) | |
| *A01N 37/46* | (2006.01) | |
| *A01N 43/90* | (2006.01) | |

(52) U.S. Cl.
CPC ............ *A01G 1/002* (2013.01); *A01G 1/00* (2013.01); *A01G 7/06* (2013.01); *A01N 37/46* (2013.01); *A01N 43/90* (2013.01)

(58) Field of Classification Search
CPC ........... A01G 1/002; A01G 7/06; A01G 1/00; A01N 43/90; A01N 37/46
See application file for complete search history.

(56) References Cited

U.S. PATENT DOCUMENTS

| 4,417,417 | A | 11/1983 | Mehra-Palta | 47/58 |
|---|---|---|---|---|
| 5,593,947 | A * | 1/1997 | Kinnersley et al. | 504/283 |
| 6,323,394 | B1 | 11/2001 | Kumar et al. | 800/278 |
| 6,389,746 | B1 * | 5/2002 | Bransby | 47/58.1 R |
| 6,995,016 | B2 | 2/2006 | Eudes et al. | |
| 7,052,912 | B1 | 5/2006 | Woods et al. | |
| 7,303,916 | B2 | 12/2007 | Marton et al. | |
| 2002/0026659 | A1 | 2/2002 | Blowers et al. | 800/298 |
| 2002/0166149 | A1 | 11/2002 | Marton et al. | 800/320 |
| 2002/0174455 | A1 | 11/2002 | Marton et al. | |
| 2008/0209598 | A1 | 8/2008 | Laine et al. | 800/323.1 |
| 2008/0282424 | A1 | 11/2008 | Marton et al. | |

FOREIGN PATENT DOCUMENTS

| CN | 1669441 A | 9/2005 |
|---|---|---|
| CN | 101326881 A | 12/2008 |
| CN | 101361483 A | 2/2009 |
| EP | 1 207 735 A1 | 5/2002 |
| WO | 99/63819 A1 | 12/1999 |
| WO | 01/03493 A1 | 1/2001 |
| WO | 02/063024 A2 | 8/2002 |
| WO | WO 02/063023 A2 | 8/2002 |

OTHER PUBLICATIONS

Piper et al. Bulletin of green section of the US Golf association. Jul. 20, 1921.*
George et al. Plant Propagation by tissue Culture 3rd edition p. 205-226 2008.*
Czakó et al., "In Vitro Propagation of Wetland Monocots for Phytoremediation," Phytoremediation Rhizoremediation, M. Mackova et al. (eds.), 217-225, 2006, Springer.

* cited by examiner

*Primary Examiner* — Annette Para
(74) *Attorney, Agent, or Firm* — Seed IP Law Group PLLC

(57) ABSTRACT

Provided are plant hormone-based growth-enhancing compositions, which comprise at least one auxin, at least one cytokinin, and at least one polyaspartic acid, and which optionally comprise at least one seaweed concentrate and at least one surfactant. Also provided are methods of propagating grass plants, including those of family Poaceae, such as the sterile grass plant *Arundo donax*, by treating the mature or immature stems of these plants with growth-enhancing compositions to stimulate the development of roots and shoots from meristematic tissues.

34 Claims, 25 Drawing Sheets

METHODS FOR VEGETATIVE PROPAGATION OF GRASS PLANTS

CROSS REFERENCE TO RELATED APPLICATIONS

This application claims the benefit under 35 U.S.C. §119(e) of U.S. Provisional Patent Application No. 61/233,713, filed Aug. 13, 2009, which is incorporated by reference in its entirety.

BACKGROUND

1. Technical Field

The present invention relates to growth-enhancing compositions and improved methods of use thereof for propagating grass plants, such as sterile grass plants, of the Class Monocotyledonae, including those of the family Poaceae.

2. Description of the Related Art

Certain monocot grass plants are useful as biomass crops, among other uses. One monocot, Arundo donax, or Giant Reed, of the Order Poales and the Family Poaceae (Gramineae), is one of the largest grasses in the world, and is an attractive, robust, perennial reed (Tucker, *J. Arnold Arb.*, 71:145-177, 1990). The very strong, somewhat woody, clustering culms, which grow from horizontal knotty rootstocks, are known to grow to a height of 8-10 meters (see, e.g., Bailey, Manual of cultivated plants: Most commonly grown in the continental United States and Canada, Rev. Ed., MacMillan, New York, (1954); and Mabberley, The plant-book: a portable dictionary of the vascular plants, $2^{nd}$ Rev., Cambridge Univ. Press, Oxford, 1997). Giant Reed is one of the largest of the herbaceous grasses and has fleshly, creeping rootstocks that form compact masses, from which arise tough fibrous roots that penetrate deeply into the soil. The culms commonly branch during the second year of growth and are hollow with walls of 2 to 7 mm thick.

The plant is known by a variety of common names, including carrizo, bamboo reed, Danubian reed, *donax* cane, Italian reed, Provence cane and Spanish reed. *A. donax* probably originated from the freshwaters of the warm regions of eastern Asia. It has been in cultivation in Asia, North Africa, and the Middle East for thousands of years and also in North and South America, Australia and South Africa, during the past century. Further information on the culture of *A. donax* can be found, for example, in U.S. Pat. Nos. 6,389,746; 7,303,916; Bell, *Ecology and management of Arundo donax, and approaches to riparian habitat restoration in Southern California*; in *Plant Invasions: Studies From North America and Europe*, Brock et al., Eds. pp. 103-113, Backhuys Publishers, Leiden (1997); Perdue, *Econ. Bot.* 12:368-404 (1958); Rossa et al., *Bot. Acta,* 111:216-221, 1998; Roys, *Ethnobotany of the Maya: The Department of Middle American Research*. M.A.R. Series Pub. 2, Tulane U., New Orleans (1931); Zahran et al., *The vegetation of Egypt*. Chapman & Hall, London (1992); and Zohary, *Plant Life of Palestine*. Ronald Press, New York (1962).

Plants from the Class Monocotyledonae, such as *A. donax*, are multipurpose plants. Giant reed, for example, has been used for over 5,000 years in making pipe instruments, and to this day remains a primary source of reeds for clarinets, organ pipes, and other woodwind instruments.

Giant reed is also used for erosion control and has great potential for use as an energy crop (see, e.g., Szabo et al., *J. Anal. Appl. Pyrolysis.* 36:179-190, 1996). The culms are also used for fishing rods, walking sticks, mats and lattices in the construction of adobe huts. Giant reed is also a source of industrial cellulose for paper and rayon making, and for the production of other polysaccharides (Neto et al., Ind. *Crops & Prods.* 6:51-58, 1997). It has also been considered as a source of pulp for the making of paper.

Giant reed grows very rapidly. When conditions are favorable, growth at a rate of 0.3 to 0.7 meter per week for several weeks is not unusual. Young culms typically grow to their full diameter within the initial growing season, but their walls increase in thickness thereafter.

Outside its native range and the Mediterranean, however, the plant is sterile; it flowers, but does not produce viable seed. Instead, it reproduces vegetatively from fragments of stems and rhizomes (see, e.g., Boose et al., *Weed Res.* 39:117-127, 1999). Hence, there have been considerable difficulties in reliably and efficiently propagating these plants.

Traditional horticultural propagation of giant reed is by division of rhizomes. However, the propagation of giant reed by either rhizome division, or by traditional seed culture, requires a significant amount of time and effort between the initiation of division, or planting, and the successful establishment of a growing plant. Moreover, conventional methods of propagation provide limited opportunity for genetic manipulation, and, in the case of seeds, do not permit genetic control of the resulting progeny. Such conventional techniques also require large areas for the production of a sufficient number of plants to be useful in programs for the production of fuel or biomass, or for use in bioremediation programs.

A number of particular propagation methods have been developed for grass plants such as sterile grass plants. Such methods include layering, stooling, root division, tissue culture, cuttage, root culture, and sectioned node culture. However, even though these methods have been widely-used over the last two decades, they are neither efficient nor cost-effective, in part because propagation cycles are too long, and only a limited number of propagules can be created in a given amount of time and a given amount of space. Also, certain of these methods lead to somalclonal variation, a serious disadvantage in operations that require clonal uniformity.

Giant reed is only one of the monocots that exhibit such multiple uses. Whether used as ornamentals, sources of energy, or as useful vehicles to carry out industrial processes, such grass-like plants are important. Accordingly, it would be useful to provide a method by which grass plants of the Class Monocotyledonae could be propagated even in areas in which plants of these genera are sterile and in a manner that would require shorter time, less effort and less area than conventional methods. The present invention provides these and other advantages.

BRIEF SUMMARY

Embodiments of the present invention relate to improved growth-enhancing compositions, comprising cytokinins and auxins, among other ingredients, and methods of use thereof, for propagating grass plants of the Class Monocotyledonae, including those of the family Poaceae. Particular embodiments relate to methods and compositions for propagating sterile grass plants. Included are methods for propagating a grass plant, comprising: (a) treating a stem of a grass plant or a segment thereof with a composition comprising: an auxin at about 1 ppm to about 10,000 ppm, a cytokinin at about 1 ppm to about 10,000 ppm, and polyaspartic acid at about 1 ppm to about 250,000 ppm; (b) harvesting the stem treated in step (a); and (c) planting the stem harvested in step (b). In certain embodiments, step (a) is performed in situ.

In certain embodiments, such as in step (a), the stem of the grass plant is an immature stem or a segment thereof. In certain embodiments, the immature stem is about 10-25 inches in height and has about 4 to 10 nodes. In certain embodiments, the immature stem is about 3 to about 6 weeks old. In certain embodiments, such as in step (a), the stem of the grass plant is a segment of mature stem.

In certain embodiments, step (b) is performed about 3 to 20 days after step (a) is performed. In certain embodiments, step (b) is performed about 14 days after step (a) is performed. In certain embodiments, the grass plant is a sterile grass plant. In specific embodiments, the sterile grass plant is an *Arundo donax* plant, or a cultivar thereof. In certain embodiments, the grass plant belongs to the family Poaceae. In certain embodiments, the grass plant is an *Arundo gigantium, Geranium sagitatum, Miscanthus x giganteus, Saccharum officianarum* or other *Saccharum* spp., *Pennisetum purpereum* plant, or a cultivar thereof.

In certain embodiments, the compositions described above further comprise a seaweed concentrate at 1 ppm to about 500,000 ppm. In certain embodiments, the seaweed concentrate is at about 100 ppm to about 1000 ppm. In certain embodiments, the seaweed concentrate is an extract from *Ascophyllum nodosum*.

In certain embodiments, the compositions described above further comprise a surfactant at 1 ppm to about 250 ppm. In certain embodiments, the surfactant is Tween 20.

In certain embodiments, the auxin is indole butyric acid (IBA), indole-3-acetic acid (IAA), naphthalene acetic acid (NAA), 4-chlorindole-3-acetic acid (4-Cl-IAA), 2-phenylacetic acid (PAA), 2,4-dichlorophenoxyacetic acid, 2-methoxy-3,6-dichlorobenzoic acid, 4-amino-3,5,6-tricholoropicolinic acid, or a mixture thereof. In certain embodiments, the cytokinin is benzylaminopurine (BA), kinetin, zeatin (Z), dihydrozeatin (DHZ) and isopentenyladenosine (IPA), ortho-topolin (oT), meta-topolin (mT), ortho-methoxytopolin (MeoT), meta-methoxytopolin (MemT), benzladenine (BA), or a mixture thereof. In certain embodiments, the polyaspartic acid is copoly-[(3-carboxypropionamide)(2-(carboxymethyl)acetamide)].

In certain embodiments, the auxin is at about 100 ppm to about 1000 ppm. In certain embodiments, cytokinin is at about 100 ppm to about 1000 ppm. In certain embodiments, the polyaspartic acid is at about 500 ppm to about 5000 ppm.

Also included are compositions for treating a grass plant in situ, comprising: an auxin at 1 ppm to about 10,000 ppm, a cytokinin at 1 ppm to about 10,000 ppm, and polyaspartic acid at 1 ppm to about 250,000 ppm. In certain embodiments, these compositions further comprise a seaweed concentrate at 1 ppm to about 500,000 ppm. In certain embodiments, the seaweed concentrate is present at about 100 ppm to about 1000 ppm. In certain embodiments, the seaweed concentrate is an extract from *Ascophyllum nodosum*.

In certain embodiments, the compositions further comprise a surfactant at 1 ppm to about 250 ppm. In certain embodiments, the surfactant is Tween 20. In certain embodiments, the auxin is indole butyric acid (IBA), indole-3-acetic acid (IAA), naphthalene acetic acid (NAA), 4-chlorindole-3-acetic acid (4-Cl-IAA), 2-phenylacetic acid (PAA), 2,4-dichlorophenoxyacetic acid, 2-methoxy-3,6-dichlorobenzoic acid, 4-amino-3,5,6-tricholoropicolinic acid, or a mixture thereof. In certain embodiments, the cytokinin is benzylaminopurine (BA), kinetin, zeatin (Z), dihydrozeatin (DHZ) and isopentenyladenosine (IPA), ortho-topolin (oT), meta-topolin (mT), ortho-methoxytopolin (MeoT), meta-methoxytopolin (MemT), benzladenine (BA), or a mixture thereof. In certain embodiments, the polyaspartic acid is copoly-[(3-carboxypropionamide)(2-(carboxymethyl)acetamide)].

In certain of the compositions provided herein, the auxin is at about 100 ppm to about 1000 ppm. In certain embodiments, the auxin is at about 100 ppm to about 300 ppm. In certain embodiments, the auxin is at about 300 ppm to about 700 ppm. In certain embodiments, the auxin is at about 700 to about 1000 ppm. In certain embodiments, the auxin is at about 200 ppm to about 400 ppm. In certain embodiments, the auxin is at about 400 ppm to about 600 ppm. In certain embodiments, the auxin is at about 600 ppm to about 800 ppm. In certain embodiments, the auxin is at about 800 ppm to about 1000 ppm. In certain embodiments, the auxin is at about 750 ppm to about 1700 ppm.

In certain of the compositions provided herein, the cytokinin is at about 100 ppm to about 1000 ppm. In certain embodiments, the cytokinin is at about 100 ppm to about 300 ppm. In certain embodiments, the cytokinin is at about 300 ppm to about 700 ppm. In certain embodiments, the cytokinin is at about 700 to about 1000 ppm. In certain embodiments, the cytokinin is at about 200 ppm to about 400 ppm. In certain embodiments, the cytokinin is at about 400 ppm to about 600 ppm. In certain embodiments, the cytokinin is at about 600 ppm to about 800 ppm. In certain embodiments, the cytokinin is at about 800 ppm to about 1000 ppm.

In certain embodiments, the auxin is IBA. In certain embodiments, the auxin is IAA. In certain embodiments, the auxin is NAA. In certain embodiments, the auxin is a mixture of IAA and NAA. In certain embodiments, the cytokinin is zeatin. In certain embodiments, the cytokinin is BA.

In certain embodiments, the polyaspartic acid is at about 500 ppm to about 5000 ppm. In certain embodiments, the polyaspartic acid is at about 500 ppm to about 1000 ppm. In certain embodiments, the polyaspartic acid is at about 1000 ppm to about 2000 ppm. In certain embodiments, the polyaspartic acid is at about 2000 ppm to about 3000 ppm. In certain embodiments, the polyaspartic acid is at about 3000 ppm to about 4000 ppm. In certain embodiments, the polyaspartic acid is at about 4000 ppm to about 5000 ppm.

Also included are methods for producing seed stems, comprising: (a) treating an immature stem of a grass plant or a segment thereof with a composition provided herein; (b) harvesting a portion of the stem treated in step (a) to produce a seed stem; (c) growing the remaining portion of the stem of step (b) into an immature stem; and (d) repeating steps (a) and (b) at least once, thereby producing seed stems. In certain embodiments, step (a) is performed in situ.

In certain embodiments, the immature stem is about 10-25 inches in height and has about 4 to 10 nodes. In certain embodiments, the immature stem is about 3 to about 6 weeks old.

In certain embodiments, step (b) is performed 3 to 20 days after step (a) is performed. In certain embodiments, step (b) is performed about 14 days after step (a) is performed. In certain embodiments, step (b) is performed prior to pseudorhizome formation. In certain embodiments, step (d) is initiated about 1-8 weeks after step (c) is performed. In certain embodiments, step (d) is initiated about 3-6 weeks after step (c) is performed.

In certain embodiments, the plant is a sterile grass plant. In specific embodiments, the sterile grass plant is an *Arundo donax* plant. In certain embodiments, the grass plant belongs to the family Poaceae. In certain embodiments, the grass plant is an *Arundo gigantium, Geranium sagitatum, Miscanthus x giganteus, Saccharum officianarum* or other *Saccharum* spp., *Pennisetum purpereum* plant, or a cultivar thereof.

Also included are stems or segments thereof of a grass plant treated in situ with a composition provided herein. Also included are immature stems or segments thereof of a grass plant, comprising at least one node that has at least one root and at least one shoot, wherein the stem is about ⅛ inch to about ¼ inch in diameter, and wherein the root to shoot mass ratio for the at least one node is about 1/1.5 to about 1.5/1. In certain embodiments, the root to shoot mass ratio for the at least one node is about 1/1. In specific embodiments, the stem or segment is from a sterile grass plant.

DETAILED DESCRIPTION

Figure 1:
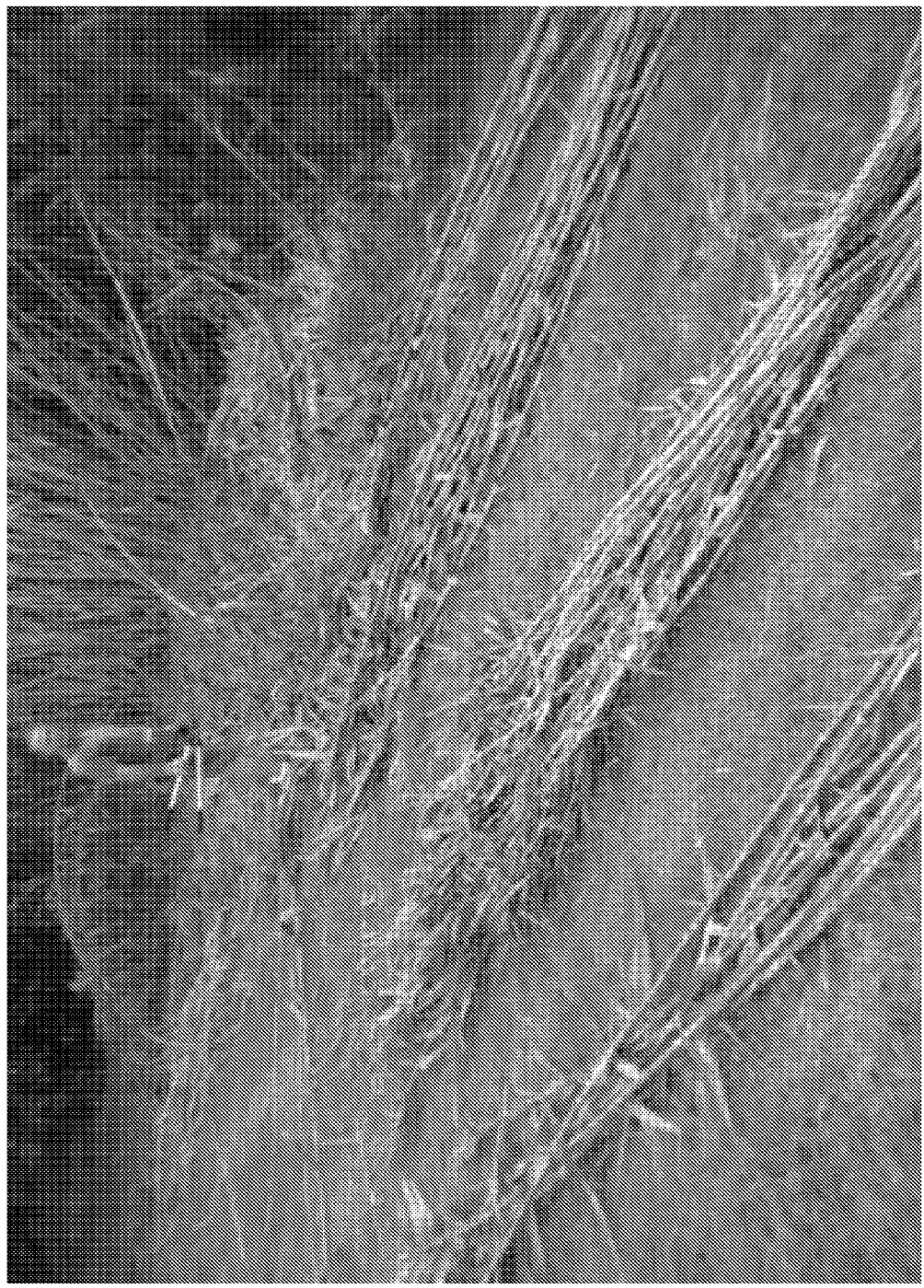
FIG. 1 shows an image of a mature culm (ramet) of a sterile grass plant.

Embodiments of the present invention relate generally to improved growth-enhancing compositions and methods of use thereof for propagating grass plants of the Class Monocotyledonae, including those of the family Poaceae. Particular embodiments relate to compositions and methods for propagating sterile grass plants, such as *Arundo donax* or its cultivars. As detailed herein, these embodiments are based in part on the discovery that the timely in situ application of growth-enhancing compositions to meristematic tissues of grass plants greatly accelerates the propagation cycle of these plants. Mainly, the improved methods of propagation provided herein include the in situ treatment of immature stems of grass plants with growth-enhancing compositions that comprise a mixture of at least one auxin, at least one cytokinin, and at least one polyaspartic acid. In certain embodiments, these compositions may further comprise at least one seaweed extract, at least one surfactant, or both.

Without wishing to be bound by any one theory, it is believed that the growth-enhancing compositions of the present invention break the dormancy of meristematic tissues at the nodes of grass plant stems, especially the nodes of immature stems, and thereby illicit shoot and root formation along the nodal margins. These stems, containing the shoots and roots formed from the otherwise latent nodes along the stem, may then be planted directly into fields to produce mature grass plants, used as seed stems in propagation beds to increase plant stock, or both, among other uses described herein and apparent to persons skilled in the art. If planted, then the treated immature stems ultimately grow into mature grass plants in less time than can be achieved by other methods.

Upon harvest, the mature grass plants may then find utility in a variety of applications. For instance, mature grass plants are useful as a source or feedstock in the production of bioenergy.

The growth-enhancing compositions and related methods of the present invention provide numerous advantages over the grass plant propagation techniques in the art. For one, the instant methods are easy to implement into existing practices, mainly because they rely on highly-effective, technically uncomplicated, non-aseptic methods that can be reproduced under normal field conditions. Also, these methods reduce or eliminate somalclonal variation, making them useful in operations that require clonal uniformity.

Further, the compositions and methods provided herein allow an extremely large number of propagules and mature plants to be created in a relatively small space, and in a relatively short time. For one, the use of juvenile or immature stems as the primary means of expanding plant stock requires little space for propagation and treatment. Also, given that portions of treated immature stems can not only be planted to produce mature stems, but can also be used as a seed stock to produce a new generation of immature stems for treatment, the methods provided herein may be used to rapidly and exponentially expand plant stock. In addition, by reducing the overall propagation cycle of grass plants by about 12 weeks, a greater amount of mature product can be produced over time.

These methods are also cost-effective. By one measurement, according to present costs, the costs of generating mature grass plants can be reduced from about $1.38/unit to about $0.03/unit. By another measurement, the cost of propagating grass plants can be reduced from about $5-6000 an acre to about $300 an acre, in part, because of the lower per-unit costs of about $0.001 per unit (or node).

Overall, by using existing rural technologies to allow planting of large acreages, the present invention may be used to readily streamline the large scale planting of grass plants such as the sterile grass plant *Arundo donax*, and thereby create a cost-effective production system for these economically valuable and useful plants.

All publications, patents and patent applications cited herein are hereby incorporated by reference in their entirety.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

Definitions

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

"Auxins" relate generally to a class of plant growth substances, also referred to as phytohormones or plant hormones, which play a central role in coordinating plant growth, and are most generally characterized by their ability to induce cell elongation in stems. However, auxins also affect other processes related to plant growth and development, such as stimulating cell division in the cambium, differentiation of the phloem and xylem, root initiation on stem cuttings, and lateral root development in tissue culture (i.e., in vitro). Auxins may also regulate the biosynthesis of cytokinins.

On a molecular level, auxins are typically characterized by an aromatic ring and a carboxylic acid group. Examples of auxins include, but are not limited to indole-3-acetic acid (IAA), indole-3-butyric acid (IBA), napthalene acetic acid (NAA), 4-chlorindole-3-acetic acid (4-Cl-IAA), 2-phenylacetic acid (PAA), 2,4-dichlorophenoxyacetic acid, 2-methoxy-3,6-dichlorobenzoic acid, and 4-amino-3,5,6-tricholoropicolinic acid.

"Cytokinins" refer generally to a class of plant growth substances (i.e., plant hormones) that stimulate cell division. Additionally, among other cellular processes, these growth substances stimulate morphogenesis (shoot initiation/bud formation) in tissue culture, stimulate the growth of lateral buds-release of apical dominance, stimulate leaf expansion resulting from cell enlargement, and promote the conversion of etioplasts into chloroplasts via stimulation of chlorophyll synthesis.

Cytokinins have been found in almost all higher plants, as well as mosses, fungi, and bacteria. Cytokinin concentrations are highest in meristematic regions and areas of continuous growth potential such as roots, young leaves, developing fruits, and seeds. These growth substances are generally believed to be synthesized in the roots and translocated via the xylem to shoots. Naturally-occurring cytokinin biosynthesis occurs mainly through the biochemical modification of adenine; hence, most cytokinins have a structure that is similar to adenine. Examples of such cytokinins include, but are not limited to, kinetin, zeatin (Z), dihydrozeatin (DHZ) and isopentenyladenosine (IPA), benzylaminopurine (BA), ortho-topolin (oT), meta-topolin (mT), ortho-methoxytopolin (MeoT), meta-methoxytopolin (MemT), and benzladenine (BA). Also included are phenylurea-type cytokinins, such as diphenylurea and thidiazuron (TDZ).

"Polyaspartic acids (PASP)" relate generally to a class of synthetic polyamides that are structural and functional analogues of the subdomains of certain biomineralization-controlling proteins. Various PASPs can be characterized and synthesized according to known techniques in the art (see, e.g., U.S. Pat. Nos. 6,380,350; 5,688,902, 5,457,176; 5,830,985; 5,391,764; 5,319,145; 5,380,817; 5,484,945; 5,756,595, each of which is incorporated by reference). PASPs are also commercially available. In certain embodiments, the polyaspartic acid is Amisorb™ (Amilar Corp. of Chicago, Ill.), also referred to as "carpramid," or copoly-[(3-carboxypropionamide)(2-(carboxymethyl)acetamide)] (see, e.g., Bernardz et al., *Journal of Plant Nutrition.* 21:2417-2427, 1998, herein incorporated by reference). Without wishing to be bound by any one theory, Amisorb™ is believed to increase nutrient uptake, mainly by translocating the other chemicals or agents (e.g., cytokinins, auxins) to the site of activation, such as meristematic tissues.

A "surfactant" as used herein relates generally to a wetting agent that lowers the surface tension of a liquid, and thereby allows easier spreading of that liquid. Surfactants are typically amphiphilic organic compounds, which contain both at least one hydrophobic groups and at least one hydrophilic group. With these characteristics, surfactants are often soluble in both organic solvents and water.

Included are ionic and non-ionic surfactants. Examples of ionic surfactants include, but are not limited to, anionic surfactants (e.g., based on sulfate, sulfonate or carboxylate anions) such as perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (i.e., sodium lauryl ether sulfate (SLES)), and alkyl benzene sulfonate; cationic surfactants (e.g., based on quaternary ammonium cations) such as cetyl trimethylammonium bromide (CTAB), cetylpyridinium chloride (CPC), polyethoxylated tallow amine (POEA), benzalkonium chloride (BAC), and benzethonium chloride (BZT); and zwitterionic or amphoteric surfactants, such as dodecyl betaine cocamidopropyl betaine, and coco ampho glycinate. Examples of non-ionic surfactants include, but are not limited to, alkyl poly(ethylene oxide), alkylphenol poly (ethylene oxide), copolymers of poly(ethylene oxide) and poly(propylene oxide) (i.e., poloxamers or poloxamines), alkyl polyglucosides such as octyl glucoside and decyl maltoside, fatty alcohols such as cetyl alcohol and oleyl alcohol, cocamide MEA, cocamide DEA, and polysorbates such as Tween 20, Tween 80, and dodecyl dimethylamine oxide.

A "seaweed concentrate" refers generally to a fertilizer that has been extracted from one or more seaweeds, including macroscopic, multicellular, and benthic marine algae, as well as members of the red, brown and green algae, among others known in the art. Certain cyanobacteria are also considered seaweeds. Typically, only the fully soluble portion of the seaweed plant is extracted, because this portion contains the desired minerals and active ingredients. Dried seaweed products include seaweed meal (e.g., crushed and dried fresh seaweed), powdered seaweed extract, which is often produced by boiling the seaweed and evaporating off its liquid content, leaving a concentrated solid extract that is powdered. Also included are liquid seaweed extracts, which are often produced from fresh seaweed by water extraction. Many seaweed concentrates are commercially available in liquid or powder forms. Examples of commercially available seaweed concentrates include, but are not limited to, Kelpak™, Sea Magic™, Natrakelp™, Alg-A-Mic™, Neptune's Harvest™, and DynaKelp™, among others known in the art. In certain embodiments, the seaweed concentrate is from *Ascophyllum nodosum*, such as Maxicrop™ (Maxicrop USA, Inc., Elk Grove Village, Ill.).

By "enhance" or "enhancing," or "increase" or "increasing," or "stimulate" or "stimulating," refers generally to the ability of one or more compositions of the present invention to produce or cause a greater physiological response in a plant, an immature stem, a mature stem, or a segment thereof, as compared to the response caused by either no composition or a control composition. A measurable physiological response may include, for example, increased tissue development (e.g., increased growth of roots or shoots or both) from nodal margins, often over a shorter time frame than otherwise, among others apparent from the understanding in the art and the description herein. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition or a control composition.

Treating a grass plant "in situ" relates to contacting an intact stem (i.e., a stem that is attached to the other portions of the plant), or a segment thereof (i.e., a section of stem that has been cleaved off from the other portions of the plant), with a composition of the present invention, such as in a climate room, a greenhouse, a float bed, a propagation bed, soil (inside or outside), etc. In situ treatment is to be contrasted with the treatment of plant cells in tissue culture.

A "grass plant," as used herein, relates to flowering plants or angiosperms of the Class Monocotyledonae, including the "true grasses" of the Poaceae family, the sedges of the Cyperaceae family, and the rushes of the Juncaceae family. The grass plants of the Poaceae family include food grains and cereals, bamboo, and the grasses of lawns and grassland. Also included within the Poaceae family are sub-families such as Anomochlooideae, a lineage of broad-leaved grasses that includes two genera (*Anomochloa, Streptochaeta*); Pharoideae, a lineage of grasses that includes three genera, including *Pharus* and *Leptaspis*; Puelioideae, a lineage that includes the African genus *Puelia*; Pooideae, including wheat, barley, oats, brome-grass (*Bromus*), and reed-grasses (*Calamagrostis*); Bambusoideae, including bamboo; Ehrhartoideae, including rice and wild rice; Arundinoideae, including giant reed and common reed; Centothecoideae, a subfamily of about a dozen genera that is sometimes included in Panicoideae; Chloridoideae, including the lovegrasses (e.g., *Eragrostis*, teff), dropseeds (*Sporobolus*), finger millet (*Eleusine coracana*), and the muhly grasses (*Muhlenbergia*); Panicoideae, including panic grass, maize, sorghum, sugar cane, most millets, fonio, and bluestem grasses; Micrairoideae; Danthonioideae, including pampas grass; and *Poa*, a genus of about 500 species of grasses native to the temperate regions of both hemispheres.

A "sterile grass plant," as used herein, relates to a grass plant that propagates by cloning or division of rhizome sections, and which does not produce a viable seed set. Illustrative examples of sterile grass plants include, but are not limited to, *Arundo donax, Arundo gigantium, Geranium sagitatum, Miscanthus×giganteus, Saccharum officianarum* and other *Saccharum* spp., *Pennisetum purpereum* plant, *Juncus* spp., *Scirpus* spp., *Cyperus* spp., *Carex* spp., *Erianthus* spp., *Typha* spp., and cultivars thereof.

A "cultivar" relates to a cultivated plant that has been selected and given a unique name because of its particular phenotype or characteristics, and is usually distinct in some manner from related plants or the plant from which it was derived. A cultivar typically retains those distinct characteristics upon propagation. The naming of a cultivar should conform to the International Code of Nomenclature for Cultivated Plants (the ICNCP, commonly known as the Cultivated Plant Code). To conform to this code, a cultivar must not only be distinct from other cultivars, but reliable to propagate in the manner prescribed for that particular cultivar, either by sexual or asexual means.

Included are grass plant cultivars from the Middle East, Hawaii, California, and the Far East, among others known in the art. Examples of *Arundo dovax* cultivars include, without limitation, the striped giant reed (*A. donax* var. *versicolor*), also known as cv. "Variegata," which has leaves with bold white stripes and grows to about 8 ft (2.4 m) tall), and the cultivar "*Macrophylla*," which has larger leaves about 3 in (7.6 cm) wide that are grayish or bluish green.

A "stem" refers to one of two main structural axes of a vascular plant, which is normally divided into "nodes" and "internodes." The term "node" refers to a joint or notch on the stem or culm at which point can be attached and above which a single nodal bud is present. The nodes typically contain buds that grow into one or more leaves, flowers, or other stems.

"Meristematic tissue" refers to a group of tissue forming cells that are capable of further development into plant organs.

A "mature" stem (or culm) of a grass plant is typically characterized by having a diameter of about ½ to about 1½ to about 3 inches or more (see, e.g., FIG. 1), though minor variants are contemplated. As used herein, a "segment" of a mature stem may be about ½, 1, 1½, 2, 2½, 3, 3½, 4, 5, 6, 7, 8, 9, 10, 11, 12, 13, 14, 15 or more inches in length, and may include at least 1, 2, 3, 4, 5, 6, 7, 8, 9, 10, or more nodes, or joints. In certain embodiments, a segment of a mature stem is about 1½ inches in length and includes one node. In certain embodiments, a segment of a mature stem is about ½ inch to about ¾ inch in diameter.

Figure 2:
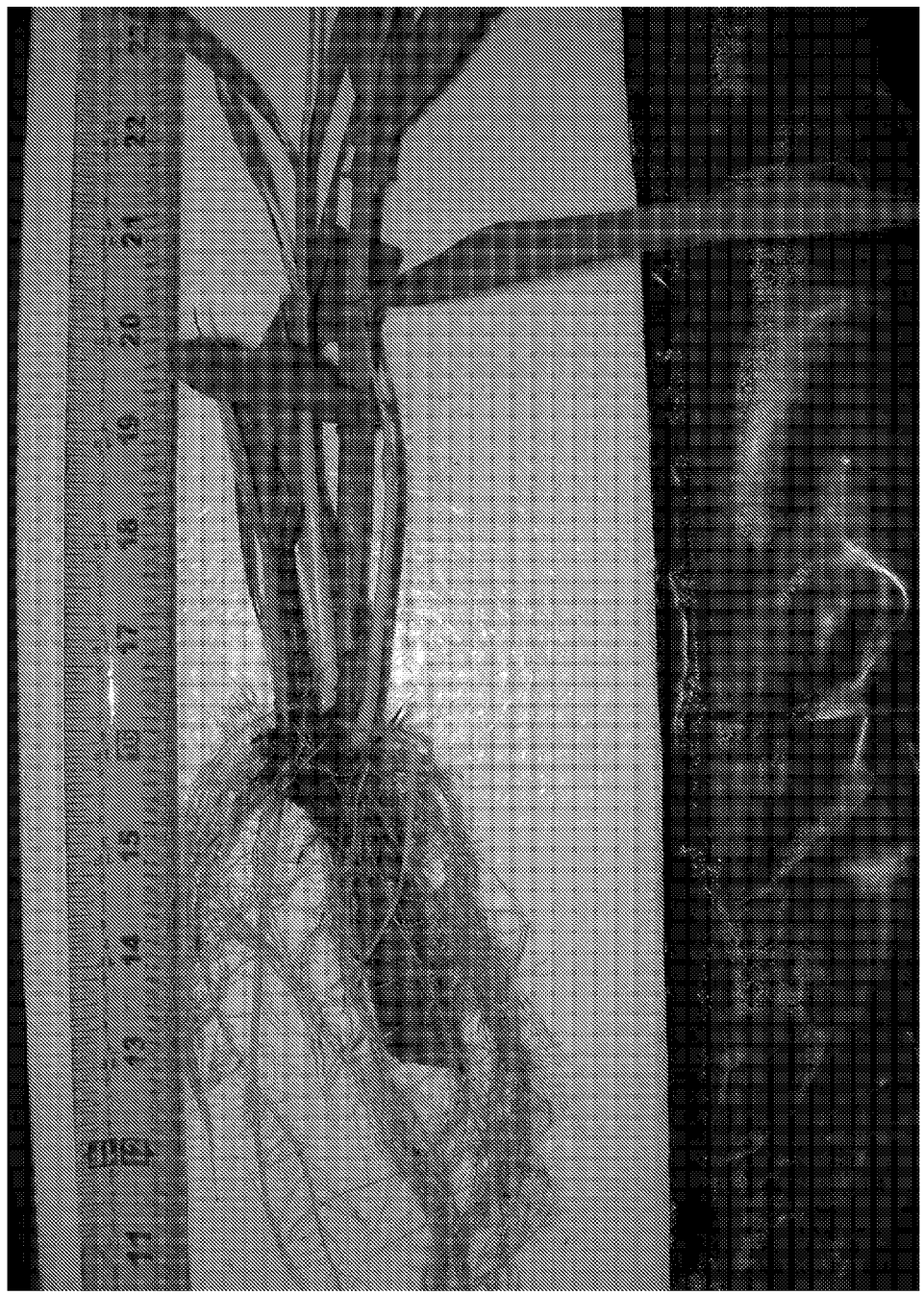
FIG. 2 shows an image of an immature stem (or ramet) of a sterile grass plant.

An "immature" stem (or ramet) of a grass plant is typically characterized by having a diameter of about ⅛ to about ¼ to about ⅜ inch, possible up to about ½ an inch (see, e.g., FIG. 2), though minor variants are contemplated. An immature stem, or a segment thereof, such as an immature stem that is ready for treatment with a composition of the invention, is typically about 6-25, 10-25, 12-16, or 15-25 inches tall (or long), including all integers in between (e.g., 6, 7, 8, 9, 10, 11, 12, 13, 14, 15, 16, 17, 18, 19, 20, 21, 22, 23, 24, 25, inches tall). An immature stem typically contains about 4 to about 10 or 12 meristematic nodal sections (i.e., nodes), including about 4, 5, 6, 7, 8, 9, 10, 11, or 12 nodes. In certain embodiments, typically depending on the desired harvesting cycle, location, or season, an immature stem may be longer than 25 inches, including up to about 6-10 feet in length (e.g., 3, 4, 5, 6, 7, 8, 9, 10, 11, 12, or more feet in length), and still maintain the diameter of an immature stem. A "segment" of an immature stem may also include a micro-segment, or a micro-node, which may be about ½, 1, 1½, 2, 2½, 3, or 3½ inches long, and which typically contains one meristematic node.

A "mother" stem or "mother" plant, as used herein, refers to whole stems or culms, or segments thereof, which may be used, often repeatedly, as planting materials to generate seed stems or seed plants. A mother plant may include, for example, a cluster of immature stems.

A "seed" stem or "seed" plant relates to an immature stem, or a portion thereof that typically contains at least one node, which is often cleaved from the upper portion of a mother plant, and which may then be planted into the soil.

A "rhizome," or "rootstalk," is a characteristically horizontal stem of a plant that is usually found underground, often sending out roots and shoots from its nodes. In vascular plants, the "root" is the organ of a plant that typically lies below the surface of the soil, though roots can also be aerial (growing above the ground) or aerating (growing up above the ground or especially above water). Typically, a root may be defined as a part of a plant body that bears no leaves, and also lacks nodes. Shoots are new, immature growths on a plant, which grow into stems, branches, or leaves.

Compositions

As noted above, embodiments of the present invention relate to growth-enhancing compositions for propagating grass plants, such as sterile grass plants, and methods of use thereof. In certain embodiments, these compositions comprise at least one auxin, at least one cytokinin, and at least one polyaspartic acid. Optionally, the compositions may further comprise at least one seaweed concentrate, at least one surfactant, or both.

Examples of auxins include, without limitation, indole-3-acetic acid (IAA), indole-3-butyric acid (IBA), napthalene acetic acid (NAA), 4-chlorindole-3-acetic acid (4-Cl-IAA), 2-phenylacetic acid (PAA), 2,4-dichlorophenoxyacetic acid, picloram, 2-methoxy-3,6-dichlorobenzoic acid, and 4-amino-3,5,6-tricholoropicolinic acid, independently, or in combinations or mixtures thereof. In certain embodiments, auxins can be present in ranges from about 1 ppm to about 10,000 ppm, including about 20-8000 ppm, about 30-7000 ppm, about 40-6000 ppm, about 50-5000 ppm, about 60-4000 ppm, about 70-3000 ppm, about 80-2000 ppm, about 100-1000 ppm, 100-2000 ppm, 100-3000 ppm, 100-4000 ppm, 100-5000 ppm, 100-6000, 100-8000 ppm, 1000-8000 ppm, 1000-7000 ppm, 1000-6000 ppm, 1000-5000 ppm, 1000-4000 ppm, 1000-3000 ppm, 1000-2000 ppm, 100-300 ppm, 300-700 ppm, 700-1000 ppm, 200-400 ppm, 400-600 ppm, 600-800 ppm, 800-1000 ppm, 1000-1200 ppm, 1200-1400 ppm, 1400-1800 ppm, 1800-2200 ppm, 2000-2200 ppm, 2200-2400 ppm, 2400-2600 ppm, 2600-2800 ppm, 2800-3000 ppm, 3000-3200 ppm, 3200-3400 ppm, 3400-3600 ppm, 3600-3800 ppm, 3800-4000 ppm, 4000-4200 ppm, 4200-4400 ppm, 4400-4600 ppm, 4600-4800 ppm, 4800-5000 ppm, 1-100 ppm, 100-400 ppm, 200-800 ppm, 300-1000 ppm, 1-500 ppm, 500-1000 ppm, 750-1700 ppm, 1000-1500 ppm, 1500-2000 ppm, 2000-2500 ppm, 2500-3000 ppm, 3000-3500 ppm, 3500-4000 ppm, 4000-4500 ppm, 4500-5000 ppm, and other ranges apparent to persons skilled in the art.

In certain embodiments, auxins can be present at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm, including all integers in between.

Certain specific compositions may include a mixture of IAA (e.g., at about 450-800 ppm, including all integers in between) and NAA (e.g., at about 300-900 ppm, including all integers in between), for a total auxin concentration of about 750 ppm to about 1700 ppm.

Certain specific compositions may include IBA (e.g., at about 200-1000 ppm, 200-400 ppm, 400-600 ppm, 600-800 ppm, 800-1000 ppm, 1000-1200 ppm, 1200-1400 ppm, 1400-1600 ppm, 1600-1800 ppm, 1800-2000 ppm, including all integers in between) as the only auxin.

In certain embodiments, the auxin is IBA at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm, including all integers in between. In certain embodiments, the auxin is IAA at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm. In certain embodiments, the auxin is NAA at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm.

Examples of cytokinins include, without limitation, kinetin, zeatin (Z) (cis and trans), dihydrozeatin (DHZ) and isopentenyladenosine (IPA), benzylaminopurine (BA), orthotopolin (oT), meta-topolin (mT), ortho-methoxytopolin (MeoT), meta-methoxytopolin (MemT), and benzladenine (BA). Also included are phenylurea-type cytokinins, such as diphenylurea and thidiazuron (TDZ). In certain embodiments, cytokinins can be present in ranges from about 1 ppm to about 10,000 ppm, including about 20-8000 ppm, about 30-7000 ppm, about 40-6000 ppm, about 50-5000 ppm, about 60-4000 ppm, about 70-3000 ppm, about 80-2000 ppm, about 100-1000 ppm, 100-2000 ppm, 100-3000 ppm, 100-4000 ppm, 100-5000 ppm, 100-6000, 100-8000 ppm 1000-8000 ppm, 1000-7000 ppm, 1000-6000 ppm, 1000-5000 ppm, 1000-4000 ppm, 1000-3000 ppm, 1000-2000 ppm, 100-300 ppm, 300-700 ppm, 700-1000 ppm, 200-400 ppm, 400-600 ppm, 600-800 ppm, 800-1000 ppm, 1000-1200 ppm, 1200-1400 ppm, 1400-1800 ppm, 1800-2200 ppm, 2000-2200 ppm, 2200-2400 ppm, 2400-2600 ppm, 2600-2800 ppm, 2800-3000 ppm, 3000-3200 ppm, 3200-3400 ppm, 3400-3600 ppm, 3600-3800 ppm, 3800-4000 ppm, 4000-4200 ppm, 4200-4400 ppm, 4400-4600 ppm, 4600-4800 ppm, 4800-5000 ppm, 1-100 ppm, 100-400 ppm, 200-800 ppm, 300-1000 ppm, 1-500 ppm, 500-1000 ppm, 750-1700 ppm, 1000-1500 ppm, 1500-2000 ppm, 2000-2500 ppm, 2500-3000 ppm, 3000-3500 ppm, 3500-4000 ppm, 4000-4500 ppm, 4500-5000 ppm, and other ranges apparent to persons skilled in the art.

In certain embodiments, cytokinins can be present at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm, including all integers in between. In certain embodiments, the cytokinin is zeatin at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm, including all integers in between. In certain embodiments, the cytokinin is BA at about 1, 10, 20, 30, 40, 50, 60, 70, 80, 90, 100, 110, 120, 130, 140, 150, 160, 170, 180, 190, 200, 215, 235, 250, 275, 295, 300, 315, 335, 350, 375, 395, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4300, 4400, 4500, 4600, 4800, 5000, 5500, 6000, 7500, 8000, 9500, or 10,000 ppm, including all integers in between.

Examples of polyaspartic acids (PASPs) include, without limitation, Amisorb™ (Amilar Corp. of Chicago, Ill.), also referred to as "carpramid," or copoly-[(3-carboxypropionamide)(2-(carboxymethyl)acetamide). One or more PASPs such as Amisorb™ may be present in ranges from about 1 ppm to about 250,000 ppm, 10-225,000 ppm, 20-200,000 ppm, 30-150,000 ppm, 40-100,000 ppm, 50-90,000 ppm, 60-80,000 ppm, 70-70,000 ppm, 80-60,000 ppm, 90-50,000 ppm, 100-40,000 ppm, 90-30,000 ppm, 100-20,000 ppm, 100-10,000 ppm, 100-5,000 ppm, 100-3,000 ppm, 200-15,000 ppm, 200-10,000 ppm, 200-5,000 ppm, 300-10,000 ppm, 400-5000 ppm, 500-5000 ppm, 500-2500 ppm, 500-1000 ppm, 5,000-25,000 ppm, 100,000-200,000 ppm, 220-1200 ppm, 1200-2200 ppm, 2200-3200 ppm, 3200-4200 ppm, 4200-5200 ppm, 1000-2000 ppm, 2000-3000 ppm, 3000-4000 ppm, 4000-5000 ppm, among other ranges apparent to persons skilled in the art. In certain embodiments, one or more PASPs may be present individually or in total at about 1, 10, 20, 30, 40, 50, 60, 70, 80, 90, 100, 120, 140, 150, 160, 180, 200, 250, 300, 350, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4200, 4400, 4500, 4600, 4800, 5000, 5500, 6000, 7500, 8000, 9500, or 10,000, 20,000, 30,000, 40,000, 50,000, 60,000, 70,000, 80,000, 90,000, 100,000, 150,000, 200,000, 250,000 ppm, including all integers in between.

In certain embodiments, seaweed concentrates may include commercially available products, such as Kelpak™, Sea Magic™, Natrakelp™, Alg-A-Mic™, Neptune's Harvest™, and DynaKelp™, among others known in the art. In certain embodiments, the seaweed concentrate is from *Ascophyllum Nodosum*, such as Maxicrop™ (Maxicrop USA, Inc., Elk Grove Village, Ill.). In certain embodiments, if present, one or more seaweed concentrates may be present in ranges from about 1 ppm to about 500,000 ppm, 10-400,000 ppm, 20-300,000 ppm, 30-400,000 ppm, 40-300,000 ppm, 50-200,000 ppm, 60-100,000 ppm, 70-90,000 ppm, 80-80,000 ppm, 90-70,000 ppm, 100-60,000 ppm, 150-50,000 ppm, 200-40,000 ppm, 250-30,000 ppm, 300-20,000 ppm, 350-15,000, 400-10,000 ppm, 450-5000, 500-2500 ppm, 500-1000 ppm, 50,000-500,000 ppm, 100,000-400,000 ppm, 200,000-300,000 ppm, 1000-3000 ppm, 1000-2000 ppm, 100-300 ppm, 300-700 ppm, 700-1000 ppm, 200-400 ppm, 400-600 ppm, 600-800 ppm, 800-1000 ppm, 1000-1200 ppm, 1200-1400 ppm, 1400-1800 ppm, 1800-2200 ppm, 2000-2200 ppm, 2200-2400 ppm, 2400-2600 ppm, 2600-2800 ppm, 2800-3000 ppm, 3000-3200 ppm, 3200-3400 ppm, 3400-3600 ppm, 3600-3800 ppm, 3800-4000 ppm, 4000-4200 ppm, 4200-4400 ppm, 4400-4600 ppm, 4600-4800 ppm, 4800-5000 ppm, 1-100 ppm, 100-400 ppm, 200-800 ppm, 300-1000 ppm, 1-500 ppm, 500-1000 ppm, 750-1700 ppm, 1000-1500 ppm, 1500-2000 ppm, 2000-2500 ppm, 2500-3000 ppm, 3000-3500 ppm, 3500-4000 ppm, 4000-4500 ppm, 4500-5000 ppm, including other ranges apparent to persons skilled in the art.

In certain embodiments, one or more seaweed concentrates, such as Maxicrop™, may be present in total at about 1, 10, 20, 30, 40, 50, 60, 70, 80, 90, 100, 120, 140, 150, 160, 180, 200, 250, 300, 350, 400, 450, 500, 600, 700, 800, 900, 1000, 1200, 1400, 1500, 1600, 1800, 2000, 2200, 2400, 2500, 2600, 2800, 3000, 3200, 3400, 3500, 3600, 3800, 4000, 4200, 4400, 4500, 4600, 4800, 5000, 5500, 6000, 7500, 8000, 9500, or 10,000, 20,000, 30,000, 40,000, 50,000, 60,000, 70,000, 80,000, 90,000, 100,000, 150,000, 200,000, 250,000, 300, 000, 350,000, 400,000, 450,000, or 500,000 ppm, including all integers in between.

Examples of surfactants include, without limitation, perfluorooctanoate (PFOA or PFO), perfluorooctanesulfonate (PFOS), sodium dodecyl sulfate (SDS), ammonium lauryl sulfate and other alkyl sulfate salts, sodium laureth sulfate (i.e., sodium lauryl ether sulfate (SLES)), alkyl benzene sulfonate, cetyl trimethylammonium bromide (CTAB), cetylpyridinium chloride (CPC), polyethoxylated tallow amine (POEA), benzalkonium chloride (BAC), and benzethonium chloride (BZT), dodecyl betaine cocamidopropyl betaine, coco ampho glycinate, alkyl poly(ethylene oxide), alkylphenol poly(ethylene oxide), copolymers of poly(ethylene oxide) and poly(propylene oxide) (i.e., poloxamers or poloxamines), alkyl polyglucosides such as octyl glucoside and decyl maltoside, fatty alcohols such as cetyl alcohol and oleyl alcohol, cocamide MEA, cocamide DEA, and polysorbates such as Tween 20, Tween 80, and dodecyl dimethylamine oxide. Surfactants may be present at about 1 ppm to about 250 ppm, 5-225, 10-200, 15-175, 20-150, 25-100, 30-175, 40-150, 50-125, 60-100 ppm, including other ranges apparent to persons skilled in the art. In certain embodiments, the surfactant, if present, is at about 1, 2, 3, 4, 5, 6, 7, 8, 9, 10, 15, 20, 25, 30, 35, 40, 45, 50, 60, 70, 80, 90, 100, 120, 140, 150, 160, 180, 200, 215, 225, 235, or 250 ppm, including all integers in between. In certain embodiments, a surfactant such as Tween 20 or Tween 80 may be added at about 1, 2, 3, 4, 5, 6, 7, 8, 9, or 10 drops per liter from a 0.1, 0.25, 0.5, 0.75, 1, 2, 3, 4, 5, 6, 7, 8, 9, 10, 15, 20, 25, 30, 35, 40, 45, 50, 60, 70, 80, 90, or 100% stock solution. A drop may be about 30, 40, 50, 60, 70, 80, 90, 100, 110, 120, 130, 140, 150 µl or more, including all integers in between, such as about 51 µl (i.e., about ⅛₀ of a teaspoon), about 62 µl, (i.e., about ¹⁄₆₀ of a U.S. fluidram or ⅛₀ of a teaspoon), about 83⅓ µl (i.e., medical drop, about ¹⁄₁₂ ml), about 99 µl (i.e., Imperial drop, about ¹⁄₃₆ of a fluidram), or about 78 µl.

Each concentration or range thereof for each specific auxin compound may be combined with each concentration or range thereof for each specific cytokinin, which may also be combined with each specific concentration or range thereof for each specific polyaspartic acid. These combinations may then be optionally combined with each concentration or range thereof for each specific seaweed concentrate and each specific surfactant.

Methods of Use

As noted above, certain embodiments of the present invention relate to improved methods of cultivating and propagating grass plants, including those of the family Poaceae, such as the sterile monocot *Arundo donax* and its cultivars. Mainly, these methods involve the timely in situ treatment of mature or immature stems, or segments thereof, with growth-enhancing compositions, as described herein. Without wishing to be bound by any one theory, it is believed that these compositions break the dormancy of meristematic tissues at the nodes of the stems, and thereby illicit shoot and root formation along nodal margins. The shoots and roots formed from these otherwise latent nodes along the stem may be planted directly into fields or used to generate seed stems in propagation or float beds (or other apparatus) to increase plant stock, among other uses described herein and apparent to persons skilled in the art.

These methods include, for example, methods for propagating a grass plant, comprising: (a) treating a stem of a grass plant or a segment thereof with a composition comprising: an auxin at about 1 ppm to about 10,000 ppm, a cytokinin at about 1 ppm to about 10,000 ppm, and polyaspartic acid at about 1 ppm to about 250,000 ppm; (b) harvesting the stem treated in step (a), and (c) planting the stem harvested in step (b). In certain embodiments, the composition may further comprise at least one seaweed concentrate at about 1 ppm to about 500,000 ppm, at least one surfactant at about 1 ppm to about 250 ppm, or both. In specific embodiments, the grass plant is a sterile grass plant.

The stem of step (a) above may be an immature stem or a mature stem, or a segment thereof, as described herein and known in the art. In certain preferred embodiments, the stem of step (a) above is an immature stem, or a segment thereof, which is typically used, for example, to either increase plant stock, or to plant directly into the soil and thereby produce a mature plant, or both. In certain embodiments, the stem in step (a) above is a mature stem, or a segment thereof, which is typically used, for example, to obtain an immature stem or a cluster of immature stems for subsequent treatment, or to plant directly into the soil and thereby produce a mature plant, or both.

Figure 3:
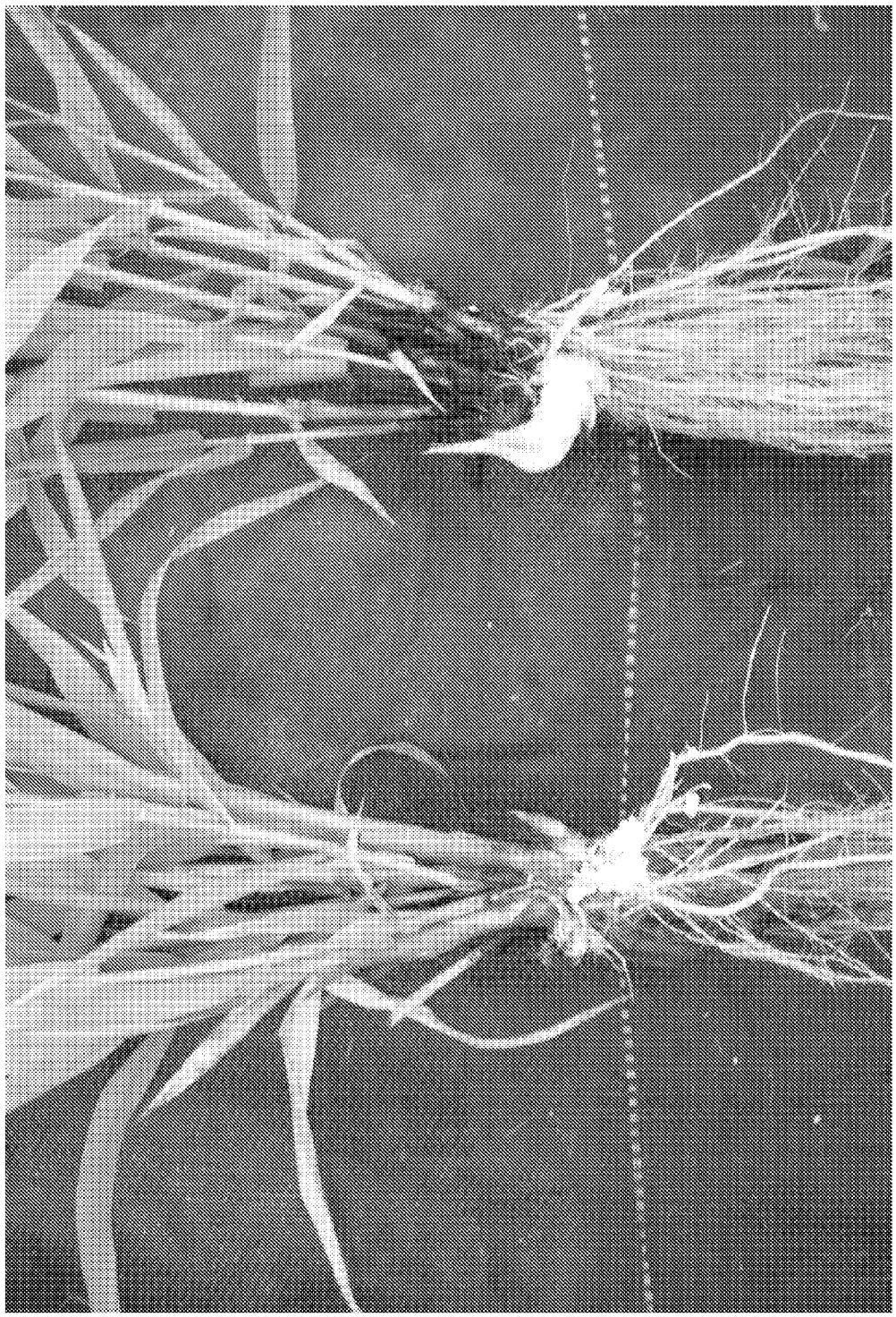
FIG. 3 shows a cluster of immature stems that were obtained from a mature stem.

For treatment in step (a) above, immature stems may be obtained according to a variety of techniques, as described herein and known in the art. As one example, immature stems or clusters of immature stems may be obtained from optionally treated mature stems or segments thereof (see FIG. 3). However, embodiments of the instant invention are not limited to obtaining immature stems by this method. In certain embodiments, for example, immature stems may be obtained directly from a juvenile plant or the juvenile stem of a mature plant, or from a previously treated immature stem (e.g., a mother stem), among other sources apparent to persons skilled in the art. These immature stems may be optionally sectioned into the desired length, placed in soil or a propagation or float bed or other apparatus, and either treated directly with growth-enhancing compositions, if ready, or incubated for a time period to allow them to grow to the desired length, and/or the develop the desired number of meristematic nodal sections, as described below.

To be ready for treatment with a growth-enhancing composition, the clusters or other sources of immature stems are typically grown until the individual immature stems are about 10-25 or 15-25 inches tall, including about 10, 11, 12, 14, 15, 16, 17, 18, 19, 20, 21, 22, 23, 24, 25 inches tall. In certain embodiments, the immature stems may have about 4-10 or 5-10 to 12 meristematic nodal stems, including about 4, 5, 6, 7, 8, 9, 10, 11 or 12 nodal stems, and are typically about ⅛ inch to about ¼ inch to about ⅜ inch to about ½ inch in diameter. This stage may be referred to as immature stem (or ramet) recruitment and proliferation, and depending on the starting material, may take, for example, about 6-15 days (including all integers in between), about 1-8 weeks, about 2-6 weeks, about 3-4 weeks, including about 1, 2, 3, 4, 5, 6, 7, or 8 weeks. Hence, at the time of initial treatment, immature stems may be about 6-15 days old or 1-8 weeks old, including 1, 2, 3, 4, 5, 6, 7, or 8 weeks old. In certain embodiments, the immature stems are about 3-6 weeks old.

After recruitment, the immature stems may then be treated with a growth-enhancing composition (see step (a) above), as described herein, such as by applying the compositions as a foliar spray until runoff, including other methods that will be apparent to persons skilled in the art. This initial may be repeated as desired. Also, the treatment with growth-enhancing compositions may be performed in an aseptic or non-aseptic environment, as desired.

Following initial treatment, and prior to harvest (see step (b) above), the immature stems may be grown or incubated for a selected time period to prepare the otherwise latent nodes (and their meristematic tissues) to illicit the desired degree of shoot and root formation, which may ultimately occur before or after planting in soil. In certain embodiments, the treated immature stems are grown for about 3 days to about 21 days, including about 3, 4, 5, 6, 7, 8, 9, 10, 11, 12, 13, 14, 15, 16, 17, 18, 19, 20, 21 days prior to harvesting. In certain embodiments, the immature stems are grown for about 14 days (about two weeks) prior to harvesting and planting.

Figure 4:
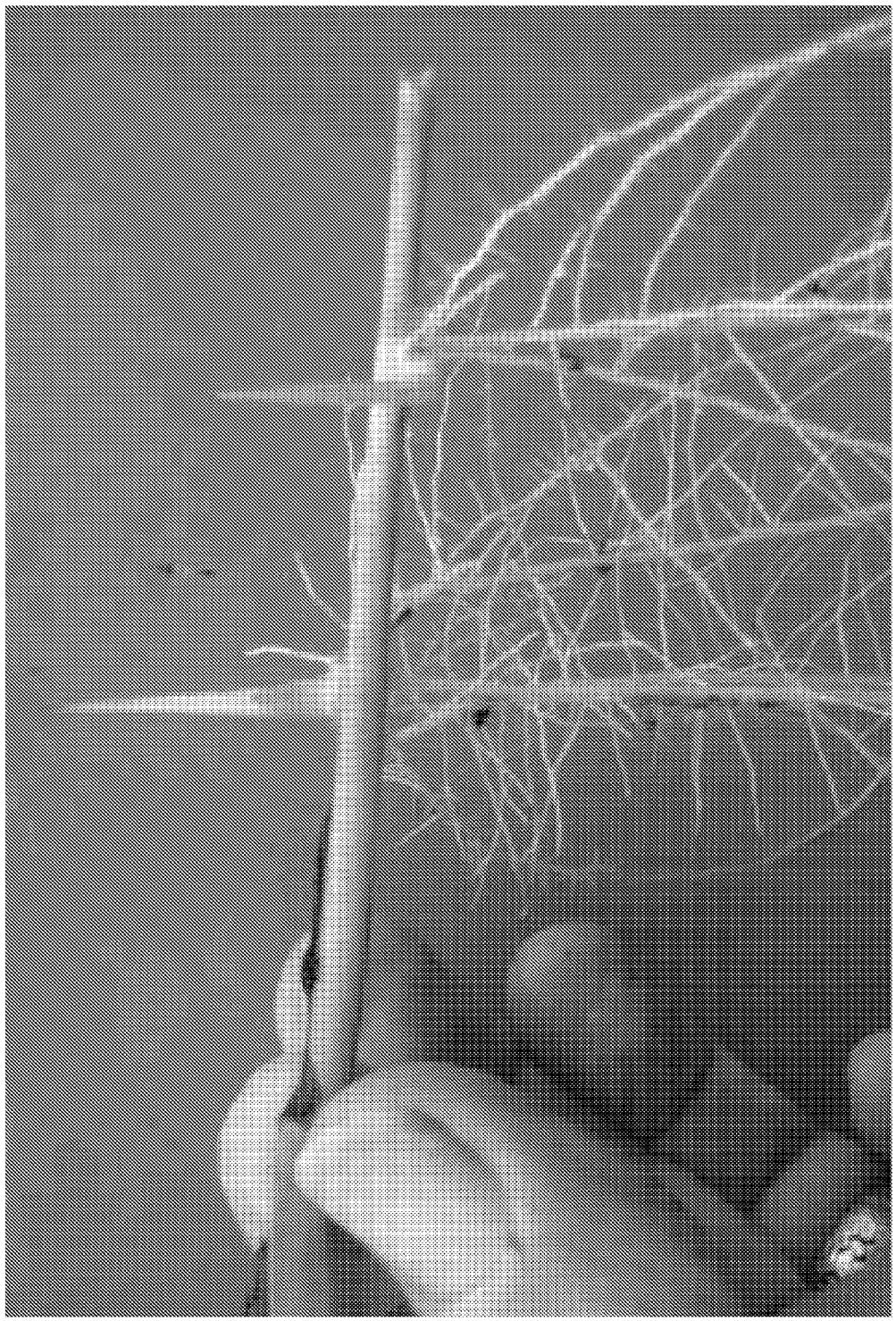
FIG. 4 shows a treated immature stem that has both roots and shoots growing from at least one of its nodes, and which is ready for harvesting.

A treated immature stem that is ready for harvesting (and planting) may have both roots and shoots growing from at least one of its nodes, or it may not yet show visible root and shoot development, but will instead illicit roots and shoots within about 3 days of planting in soil, if not before (see FIG. 4). In certain embodiments, the root to shoot mass ratio for a given node of a treated immature stem is about 1:1, but may also be about 1.1/1, 1.2/1, 1.3/1, 1.4/1, 1.5/1, 1/1.1, 1/1.2, 1/1.3, 1/1.4, or 1/1.5. In contrast to treated immature stems, the otherwise latent nodes of untreated immature stems develop only shoots, and contain no roots, either before or after planting. These untreated immature stems die after planting in soil. The treated immature stems often grow into full-size plants within about 12 months.

Figure 5:
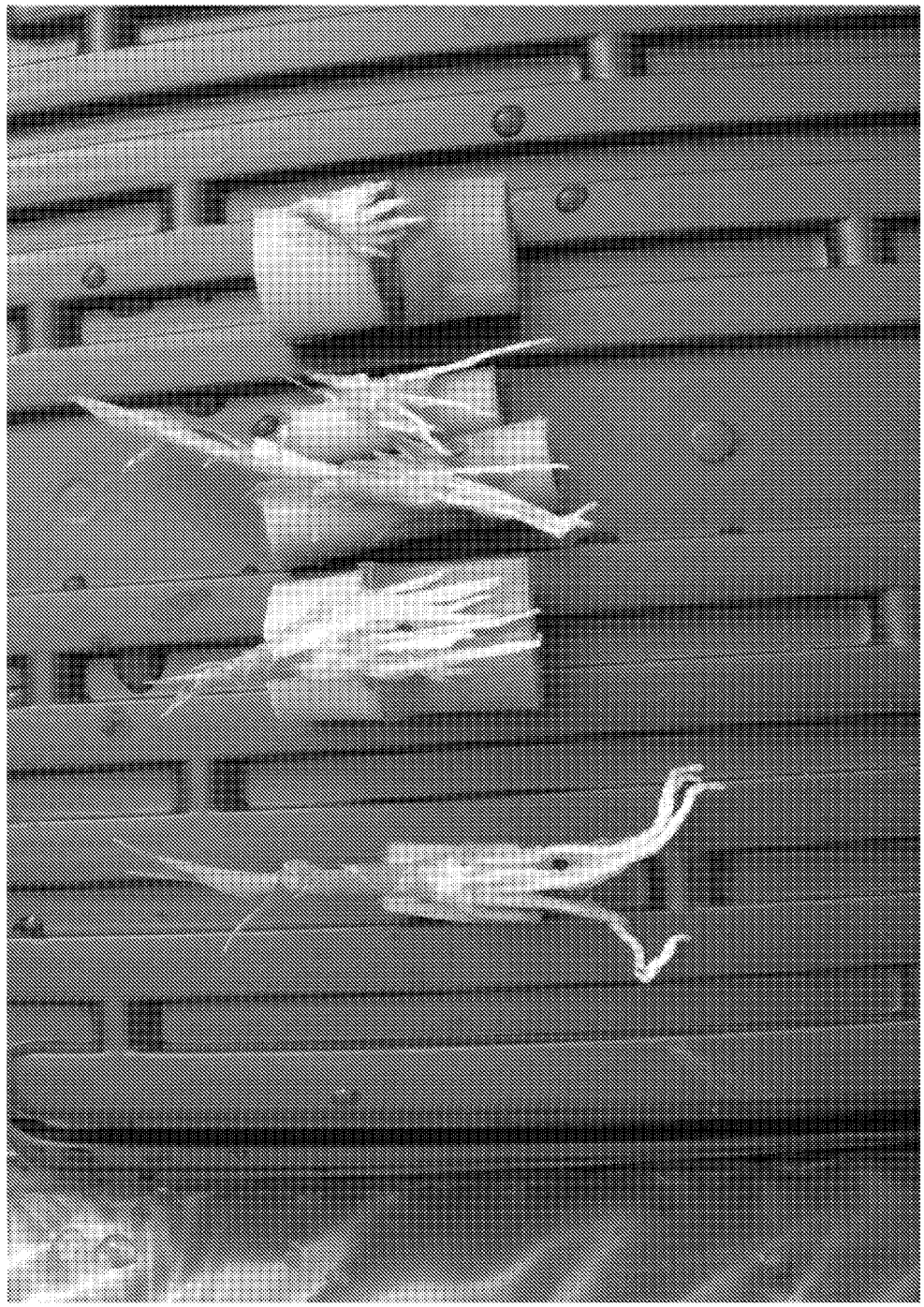
FIG. 5 shows a mature stem that has been treated to obtain a cluster of immature stems. Roots and shoots can be seen growing from the node of the treated mature stem.

As noted above, the instant methods also include the in situ treatment of mature stems of a whole or partial plant, or sectioned nodes of a mature stem. These embodiments are used mainly to obtain immature stems, which can then be further treated according to the methods provided herein. In certain embodiments, however, treated mature stems or segments thereof may be planted directly into the soil to produce a mature plant. In certain embodiments, a mature stem or a segment thereof may be optionally treated to obtain a cluster of immature stems (see FIG. 5). In one preferred embodiment, a cluster of immature stems is obtained via ramet recruitment using mature stems as a starting material, mainly via a float bed technique and treatment with a growth-enhancing composition, as described herein.

Figure 6:
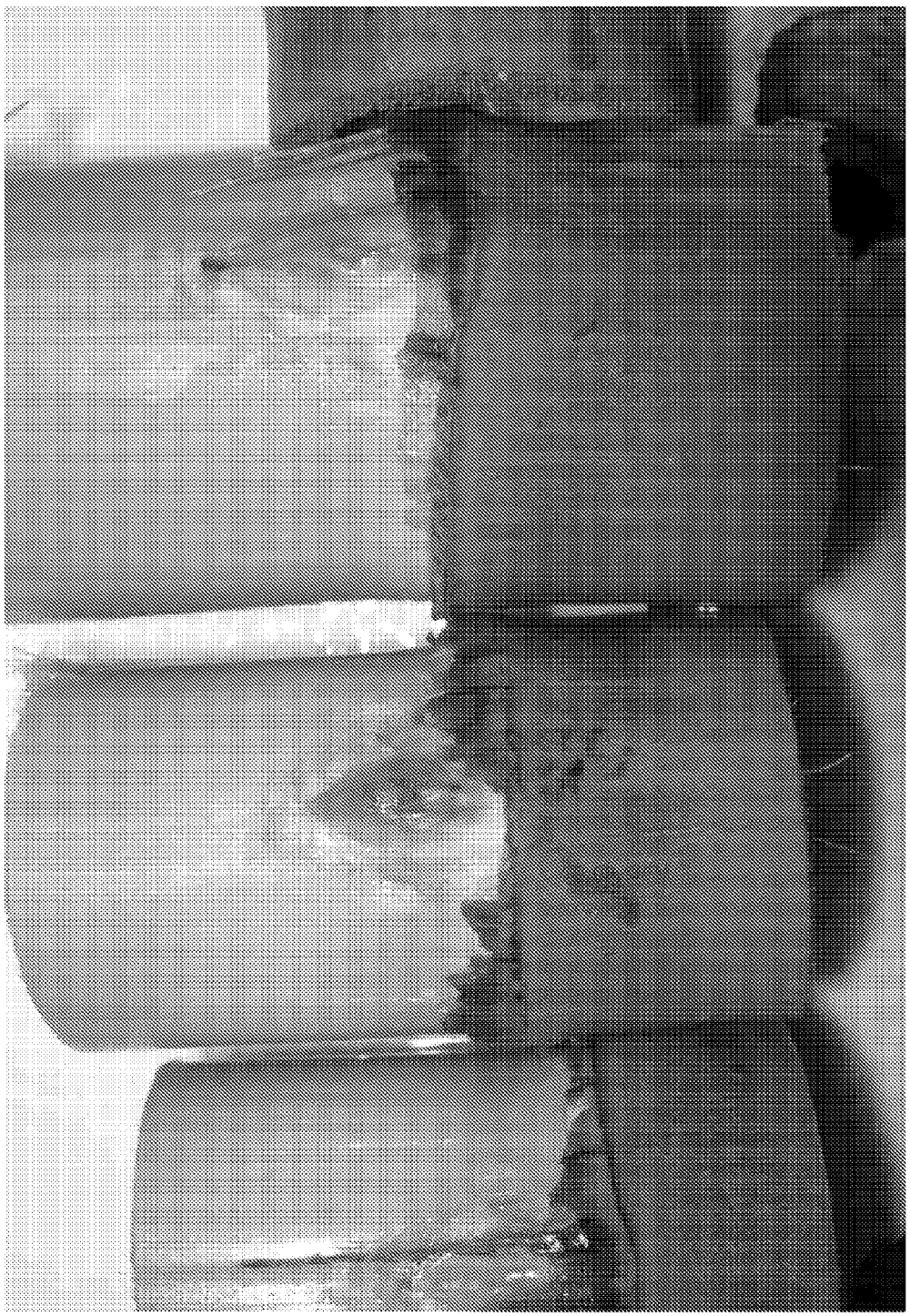
FIG. 6 shows a mature stems that have been cut into sectioned nodes or segments.

As one illustrative example of producing immature stems from mature stems, or preparing mature stems for planting, mature stems may be cut into sectioned nodes or segments, such as a segment that is about ½ inch in diameter (depending on the diameter of the stem) and about 1 inch to about 1½ inches to about 2 inches to about 3 inches long, or longer, and which contains at least one node (see FIG. 6). In certain embodiments, wild plants or cultivars of a grass plant such as *A. donax* may be harvested, cut into nodal sections or segments, and surface disinfected or sterilized with quarternary ammonium. Alternative sterilization techniques may be employed, if desired, such as by immersing the stems in 10% v/v ethanol and 0.1% Tween 80 for about 15 minutes, followed by washing with sterile water. Although not required, sterilization may reduce environmental bacteria contamination. These segments may then be inserted into a float bed (see, e.g., U.S. Pat. No. 7,052,912, herein incorporated by reference) or other apparatus to encourage shoot elongation, and incubated with an appropriate medium.

Typically, and merely by way of illustration, the conditions of a float bed system involve maintenance of temperature at about 60° F. to about 80° F., water with fertilizer (such as NPK with minor amounts of iron, zinc, manganese, copper boron, molybdenum and sulfur), and optionally rooting hormones (depending on the requirements of the plant or clone used). Such rooting hormones include, for example, indoleacetic acid, 1-naphthaleneacetic acid, and indole-3-butyric acid. Auxins may be used with or without cytokinins in the rooting stage. NM, for example, is generally used in plant culture in a concentration of between 0.1 to 10 mg/l, more preferably not exceeding about 3 mg/l. The particular auxin and its exact concentration will depend on the clone of *Arundo donax* or other grass plant being cultured, and these concentrations of IAA, NAA and IBA can be determined experimentally. The pH of the of the fluid in the float bed is typically about 4.5 to about 7.5, preferably about 6.5. In certain embodiments, de-ionized water may be used for incubating the mature stem segments in the float bed.

In certain embodiments, the mature stems or segments thereof may be optionally treated with a growth-enhancing composition, as described herein, to further stimulate root initiation, and to stimulate root and shoot development and proliferation. Even though the treatment of mature stems is optional, it may provide improved vitality, as measured by simultaneous or near-simultaneous root and shoot growth. For instance, it has been shown that treating mature stems with growth-enhancing compositions during this stage improves vitality from about 30% to about 70%, 75%, 80%, 85%, 90%, 95%, or 100%. In certain embodiments (e.g., about 1-8 weeks), these treated mature stem segments typically produce a cluster of immature stems that may be treated according to the methods provided herein. Alternatively, in certain embodiment, due partly to their increased vitality, treated mature stems may planted directly into the soil to produce a mature plant, typically about 3-21 days (e.g., about 14 days) days or weeks following initial treatment with growth-enhancing compositions, and can produce a mature plant within about 8 months.

An exemplary air temperature range for growing the mature or immature stems is from about 15° C. to about 35° C., or from about 20° C. to about 30° C., or from about 24° C. to about 28° C. The mature or immature stems may also be grown at about 25° C. In certain embodiments, immature and mature stems can be incubated in de-ionized water or mineral based soil prior to and following exposure to growth-enhancing compositions.

Figure 7:
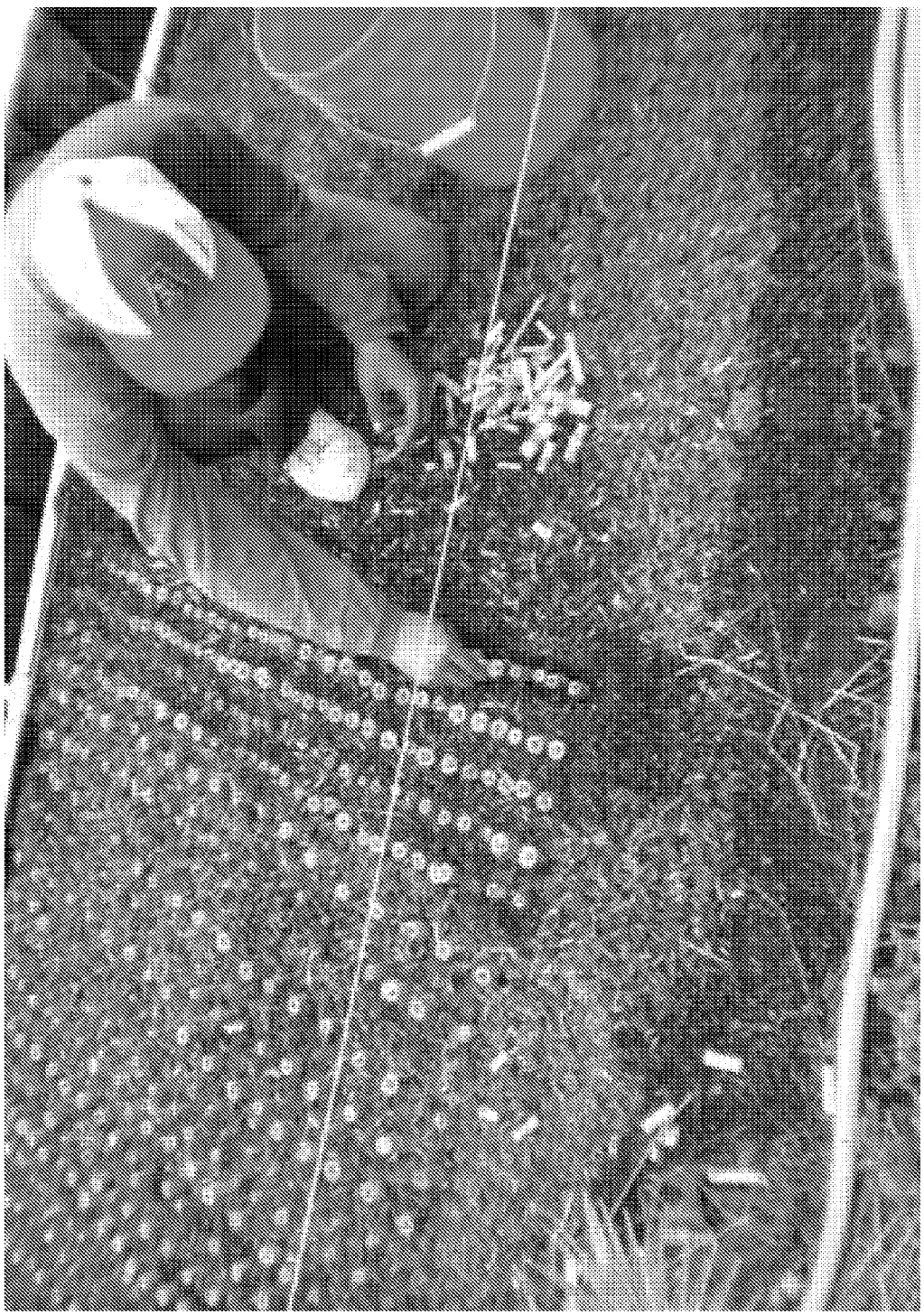
FIG. 7 shows treated mature nodal sections being hand-planted into soil.

After harvesting, treated immature or mature stems may then be planted according to techniques known in the art. Mechanized systems or hand planting systems or both are contemplated, among other techniques (see FIG. 7). Alternatively, in certain embodiments, the treated immature stems can stored (sectioned or un-sectioned), such as for shipment, and planted at a later time.

Figure 8:
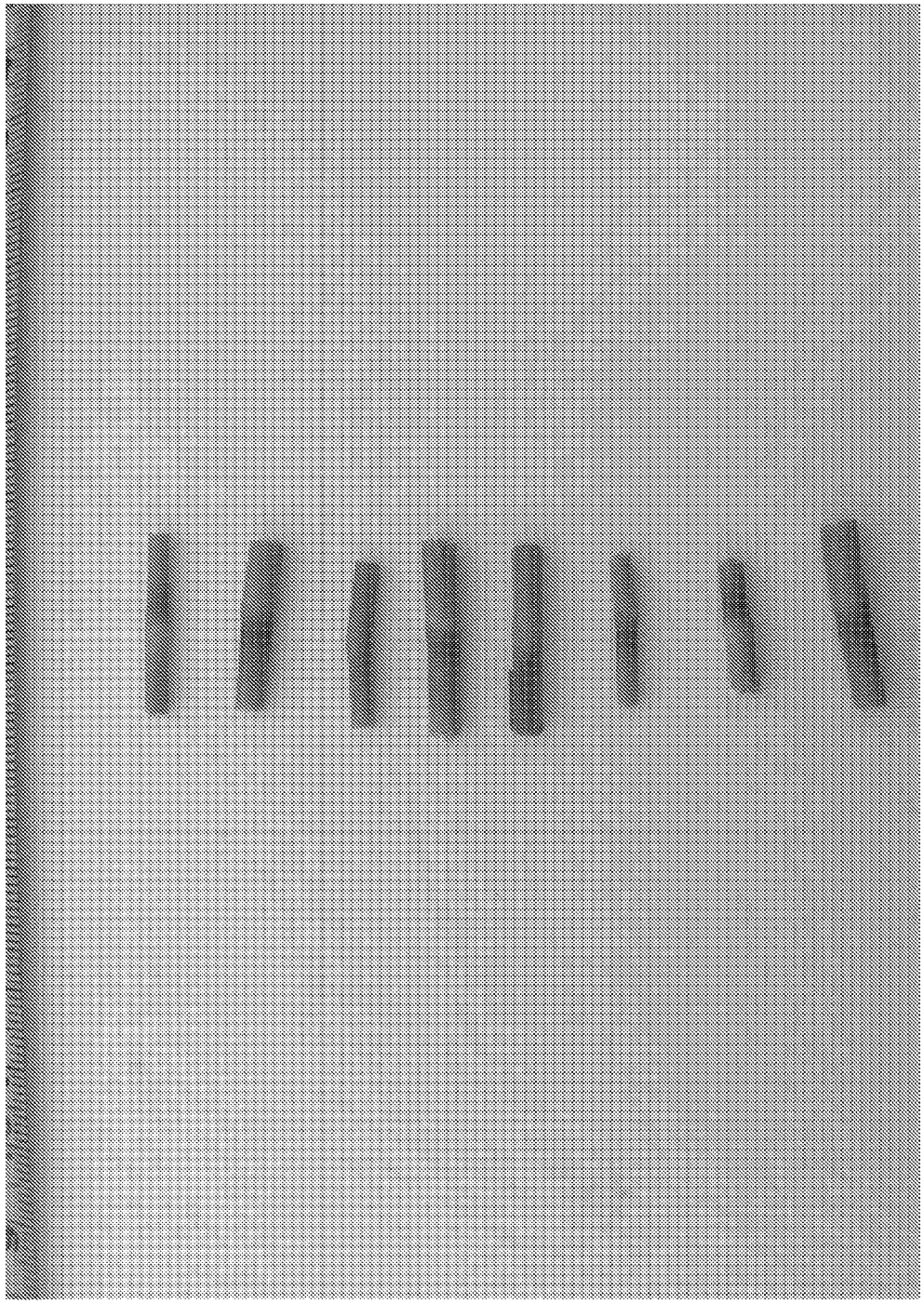
FIG. 8 shows sectioned immature ramets, or micro-nodes.
Figure 9:
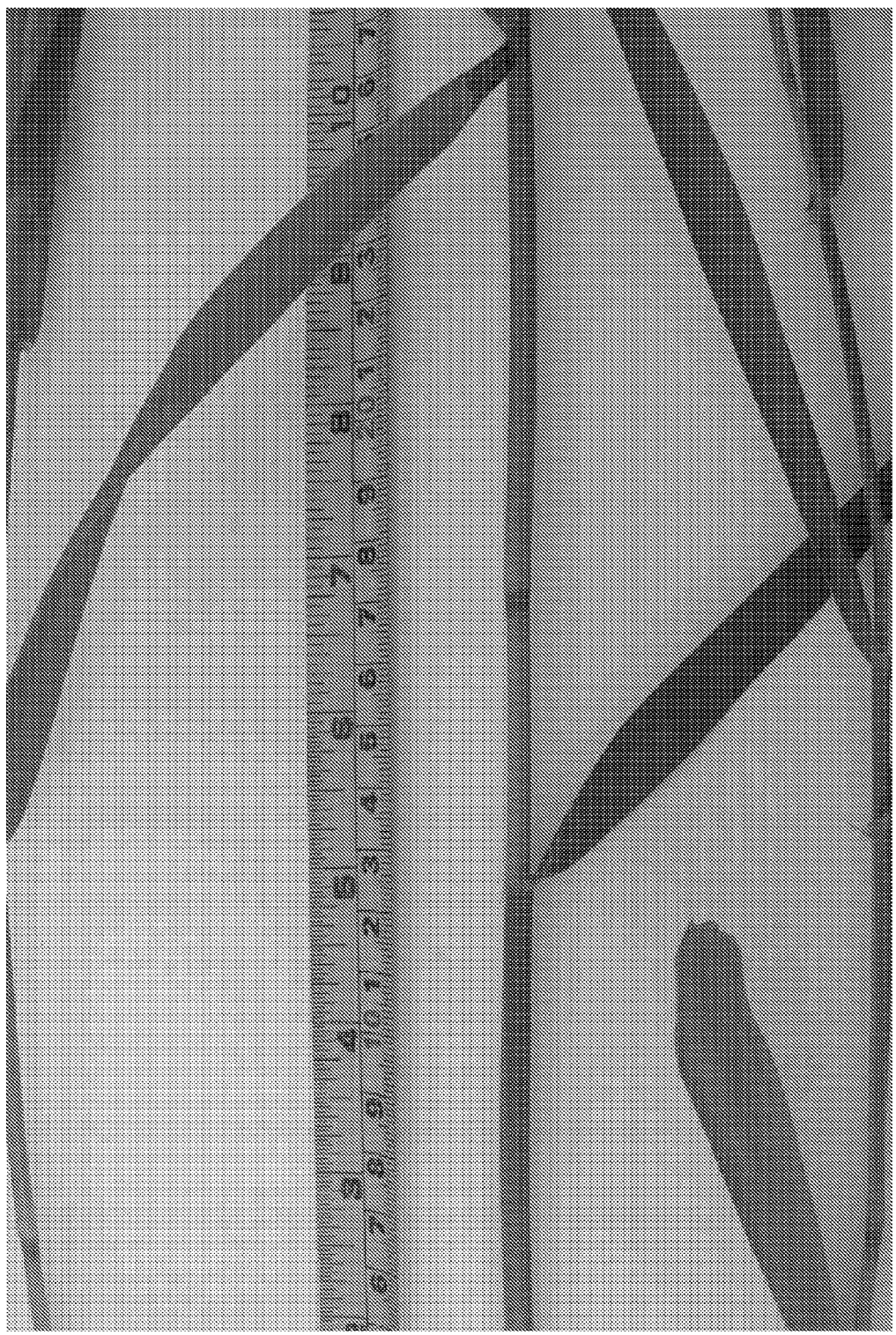
FIG. 9 shows immature stems (or ramets) prior to sectioning.

In certain embodiments, the treated stems may be planted directly into soil, such as in a field, or in a container. In certain embodiments, the treated stems may be planted whole, or first sectioned into smaller pieces to facilitate planting, including pieces about ½ inch to about 1½ inch to about 2½ inches to about 3 inches to about 4 inches or more in length (see FIGS. 7 and 8). Typically, the sectioned pieces comprise at least one node, sometimes a node that has both roots and shoots prior to planting, or sometimes a node that is capable of producing roots and shoots within a few days of planting. In certain embodiments, treated stems or segments thereof may be planted directly into soil without any further treatments, e.g., sterilization or cleaning, and without any phytosanitary concerns, because there are typically no soil particles attached to the stems. Or, if desired, the treated stems may first undergo a post-harvest (pre-planting) treatment of wax-containing fungicides, mainly to retard desiccation and inhibit fungal growth. In certain embodiments, such as immediately prior to planting, the treated stems or nodes may be further treated with a growth composition, such as an auxin/cytokinin/seaweed concentrate/polyethylene glycol (PEG) containing composition.

Merely by way of illustration, and without limitation, treated stems or sections thereof may be placed horizontally into soil (e.g., in a field or container) at depths ranging from about ¼ inches to about 6 inches below the soil surface, including depths about 1 to about 3 inches below the surface, and in rows with centers ranging from continuous to about 8 inches on center. In certain embodiments, row spacing can be contiguous to about 8 inches on center. Other planting methods will be apparent to persons skilled in the art.

In certain embodiments, instead of planting the treated stems into soil, these stems may be harvested, trimmed or sectioned into pieces that contain at least one or two or three or more nodes, and then planted or grown in a propagation bed or other apparatus (e.g., float bed). Among other uses, these embodiments may be used to increase or amplify plant stock, and relate in part to methods of producing seed stems, comprising (a) treating an immature stem of a grass plant or a segment thereof with a composition comprising: an auxin at about 1 ppm to about 10,000 ppm, a cytokinin at about 1 ppm to about 10,000 ppm, and polyaspartic acid at about 1 ppm to about 250,000 ppm; (b) harvesting a portion of the stem treated in step (a) to produce a seed stem; (c) growing the remaining portion of the stem of step (b) into an immature stem; and optionally (d) repeating steps (a) and (b) at least once, thereby producing seed stems. In certain embodiments, the composition may further comprise at least one seaweed concentrate at about 1 ppm to about 500,000 ppm, at least one surfactant at about 1 ppm to about 250 ppm, or both.

Merely by way of illustration, the immature stems in step (a) above may be first obtained by growing optionally treated mature stems in a float bed for about 1-8 weeks, as described herein, though other methods may be utilized, such as by trimming or sectioning a previously treated immature stem. Following treatment with a growth-enhancing composition, as in step (a) above, the portion of the treated immature stem in step (b) above may be harvested at the appropriate time (e.g., about 3-21 days post-treatment), according to various exemplary methods.

Figure 10:
FIG. 10 shows an image of a pseudorhizome.
Figure 11:
FIG. 11 shows root and shoot proliferation to form a cluster of immature stems that formed from the mature stem (in a float bed).
Figure 12:
FIG. 12 shows a cross section of a float bed system to illustrate root development in clusters of immature stems.
Figure 13:
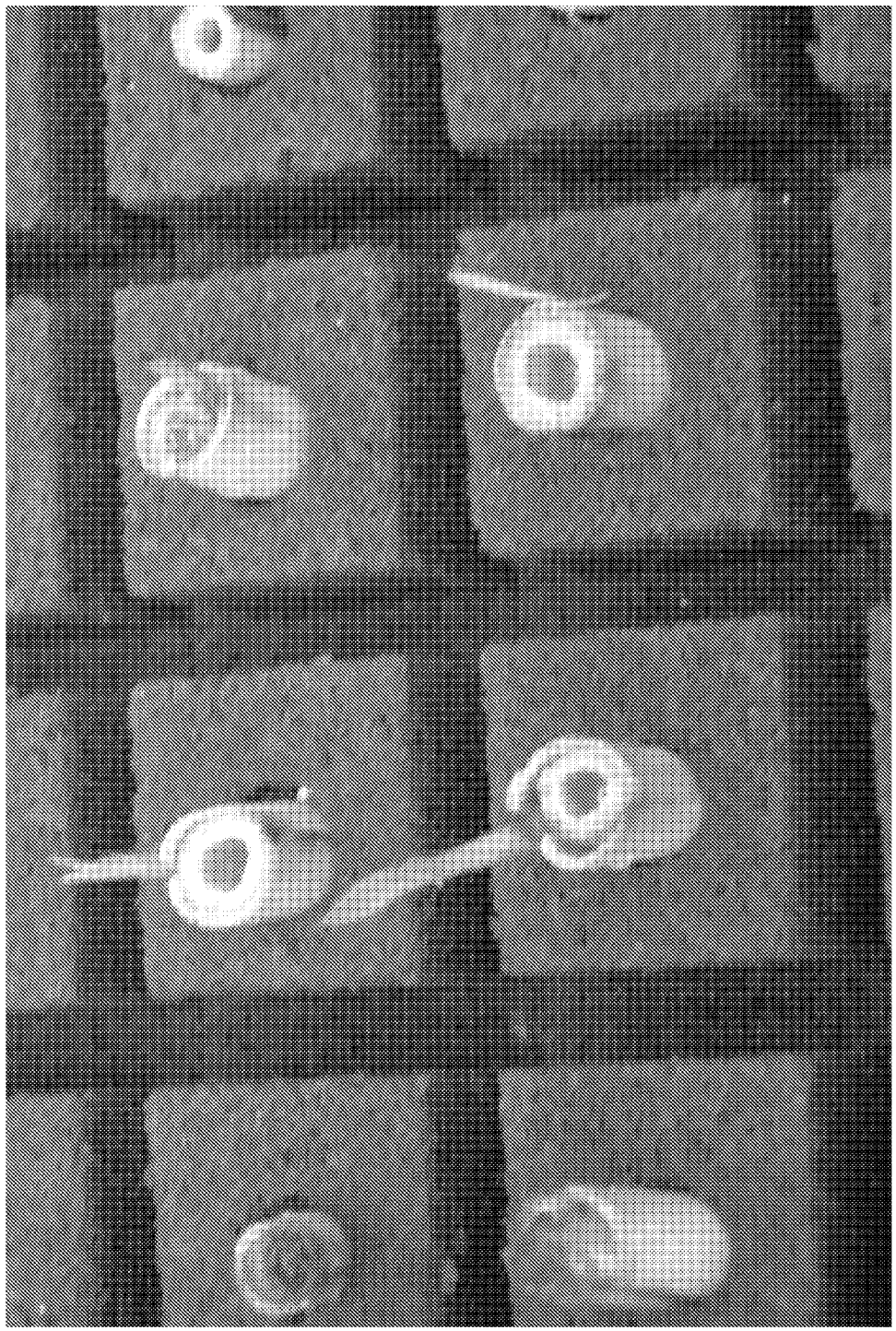
FIG. 13 shows micro-node shoot development in a propagating tray—minimal roots.
Figure 14:
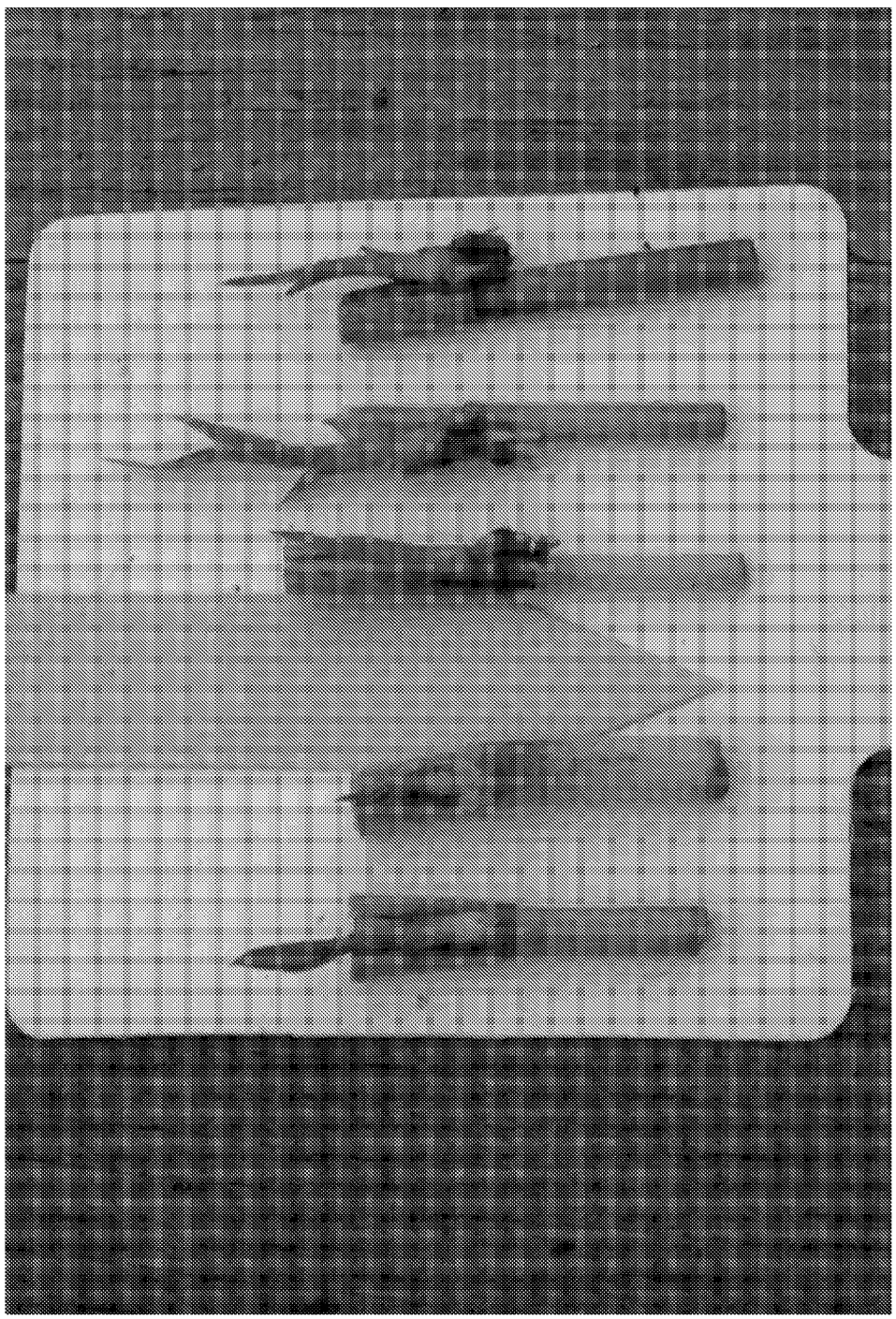
FIG. 14 shows a comparison of untreated micro-nodes with shoot development but without roots (left of yellow); and treated micro-nodes with both shoots and roots (right of yellow).
Figure 15:
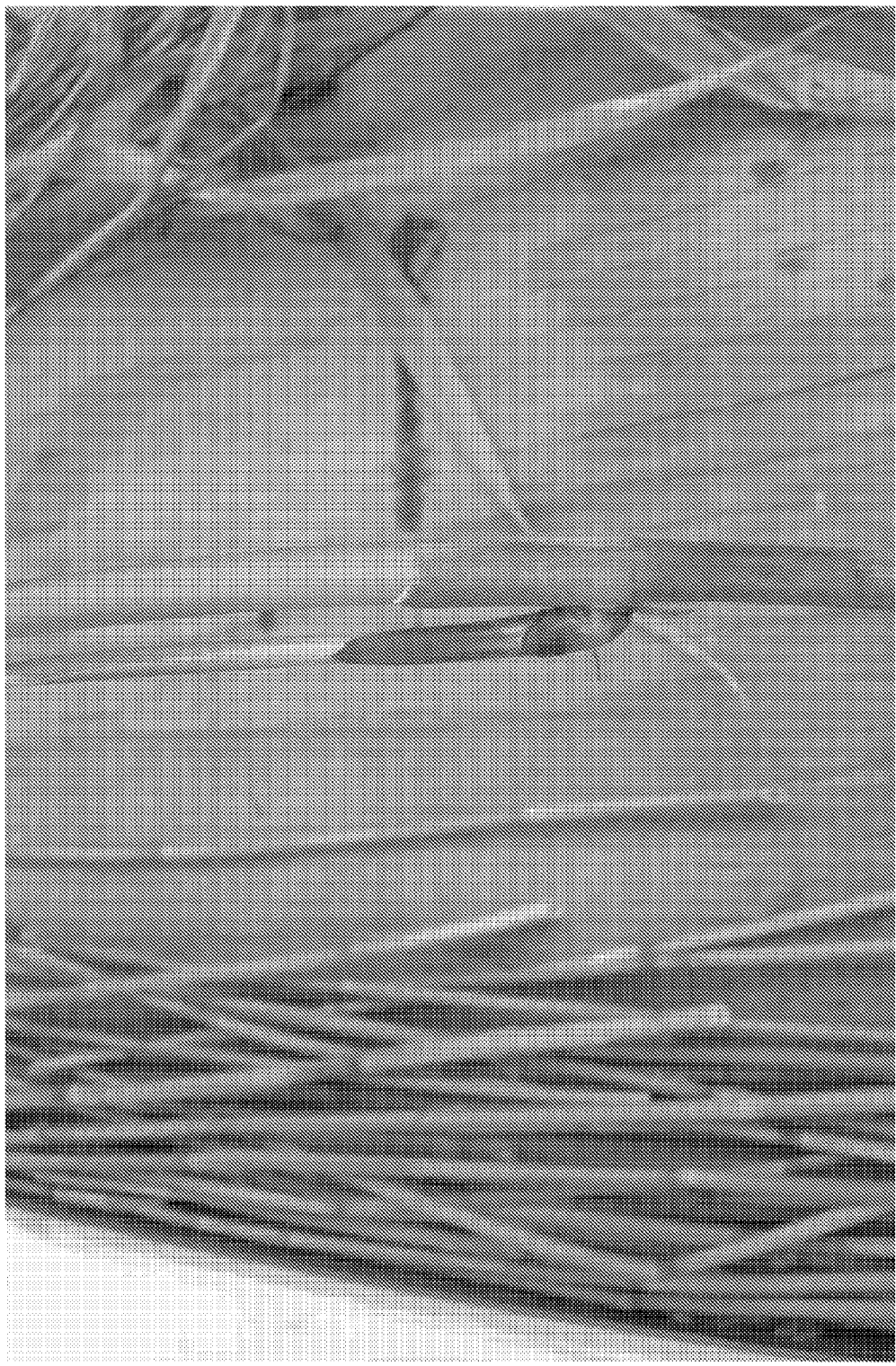
FIG. 15 shows immature stems (or ramets) that have been treated with an auxin/cytokinin mixture, and which show both shoot and root development.
Figure 16:
FIG. 16 shows immature stem (or ramet) clusters in float beds prior to harvesting. These clusters had about 6-10 individual stems with about 5-8 nodes in each stem.
Figure 17:
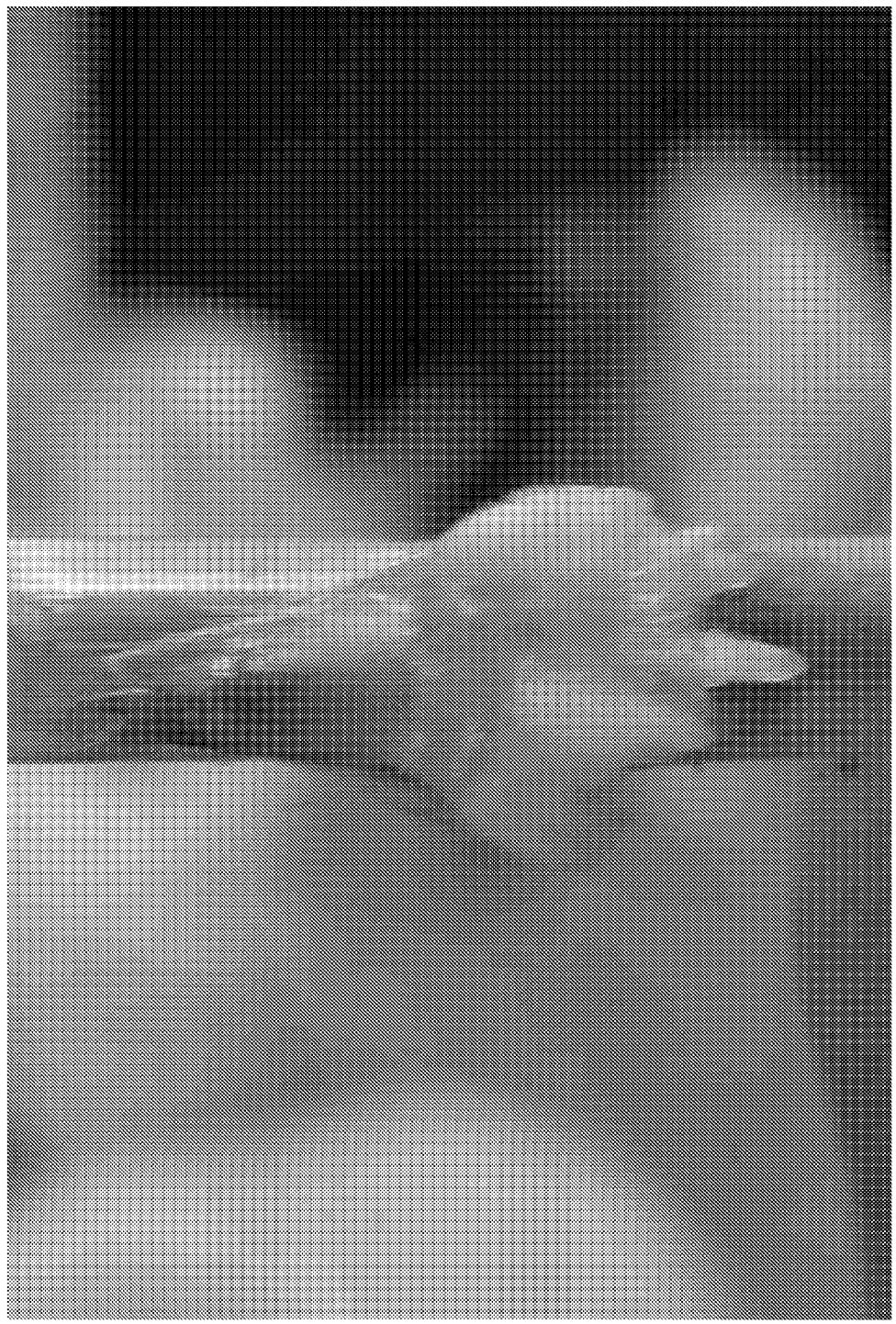
FIG. 17 shows a treated micro-node (from immature stems) showing bearded root development.
Figure 18:
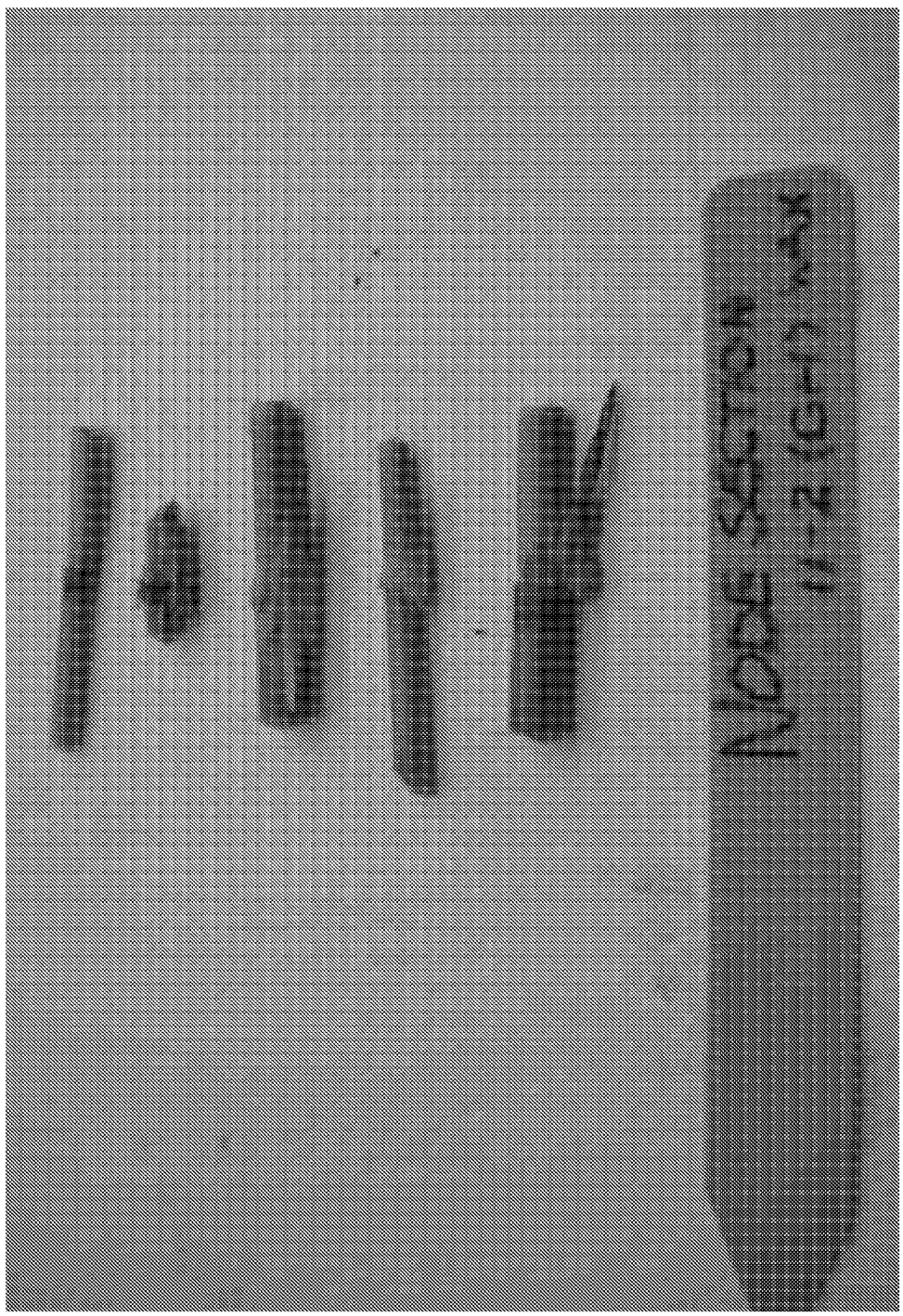
FIG. 18 shows nodes that have been sectioned from treated immature stems (or ramets), and which have both shoots and roots.
Figure 19:
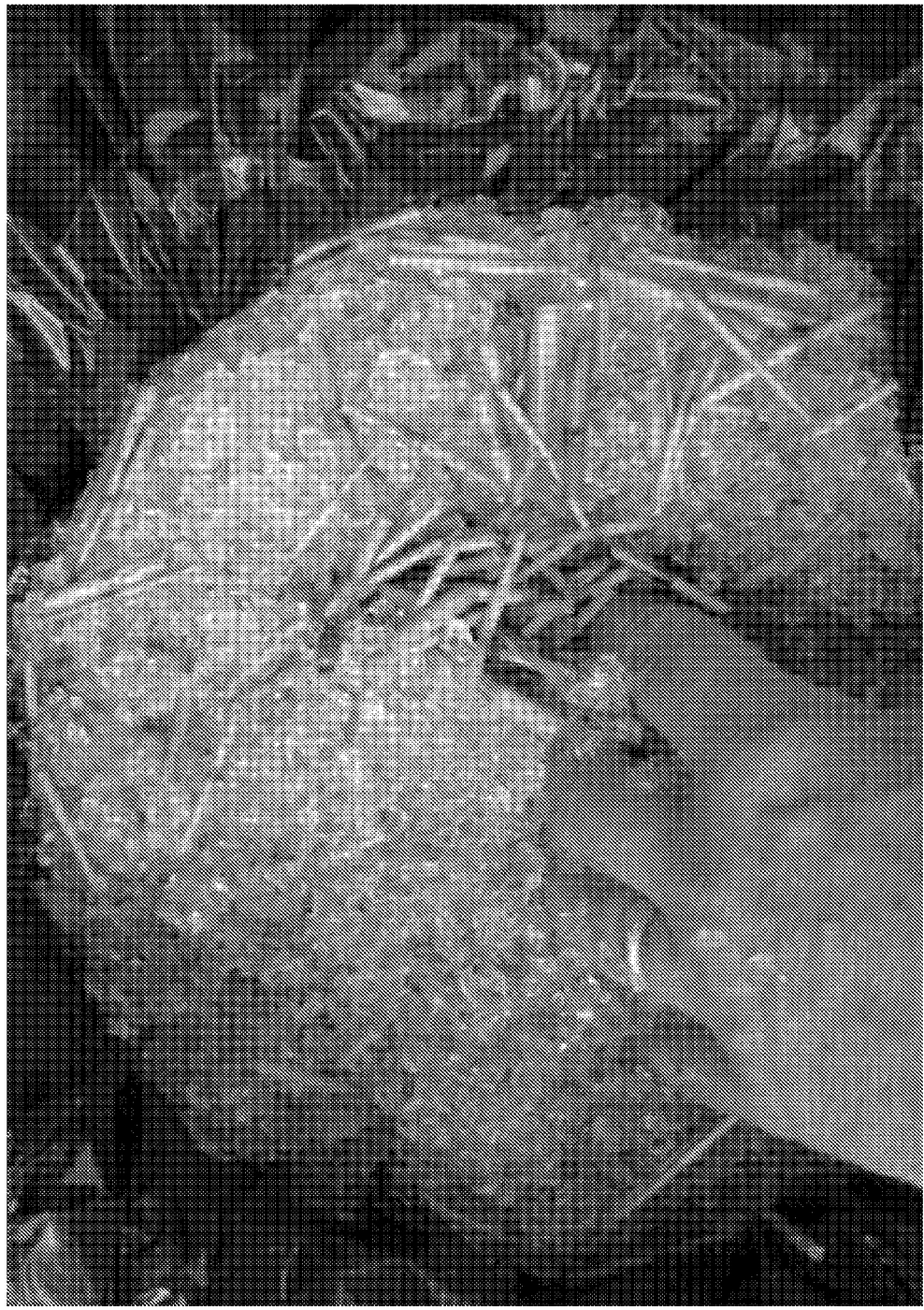
FIG. 19 shows Machias nodes being treated with auxin/cytokinin/seaweed concentrate/PEG prior to planting.
Figure 20:
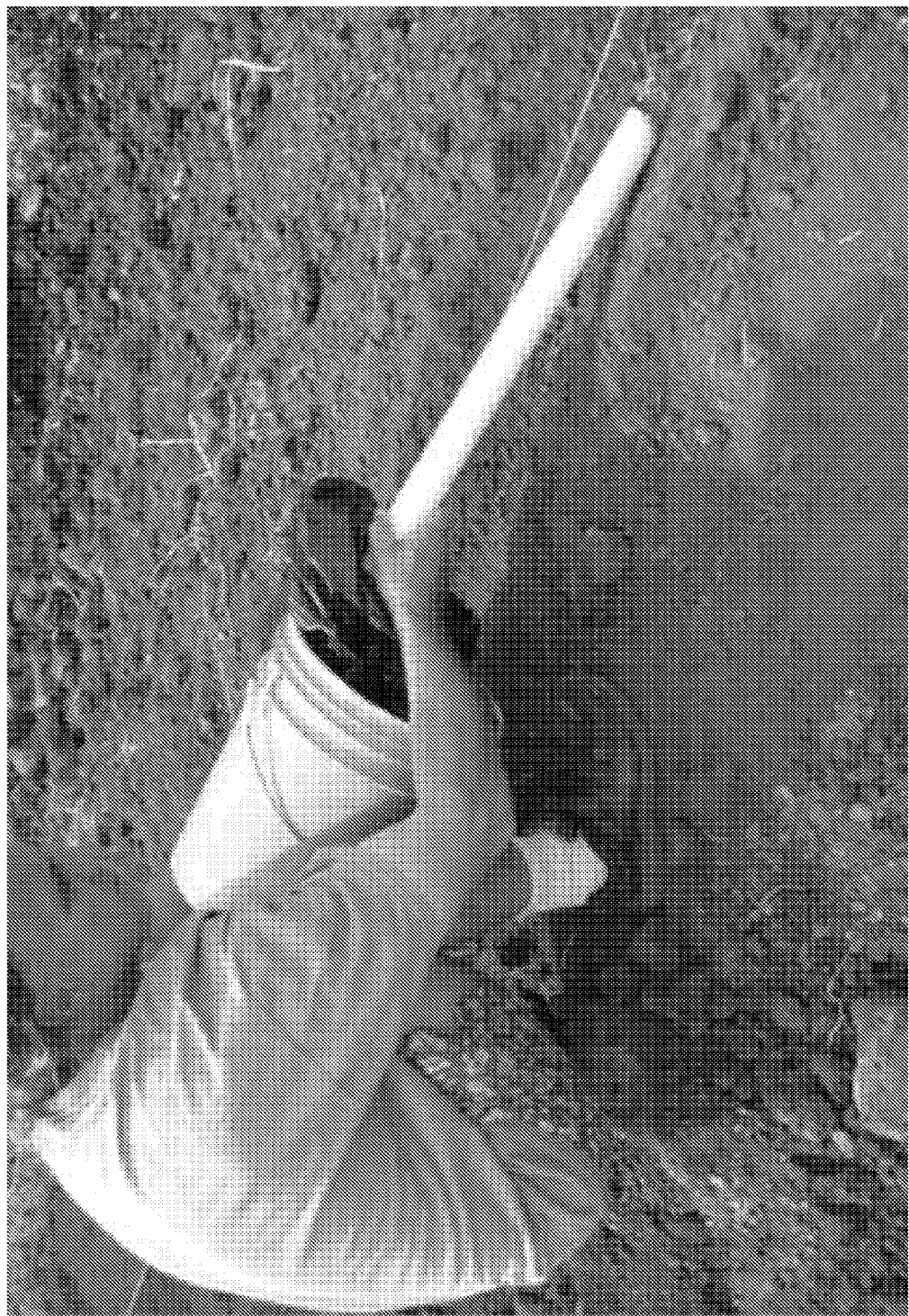
FIG. 20 shows the process of injecting treating micro-nodes into the soil with a subsoil planting shank.
Figure 21:
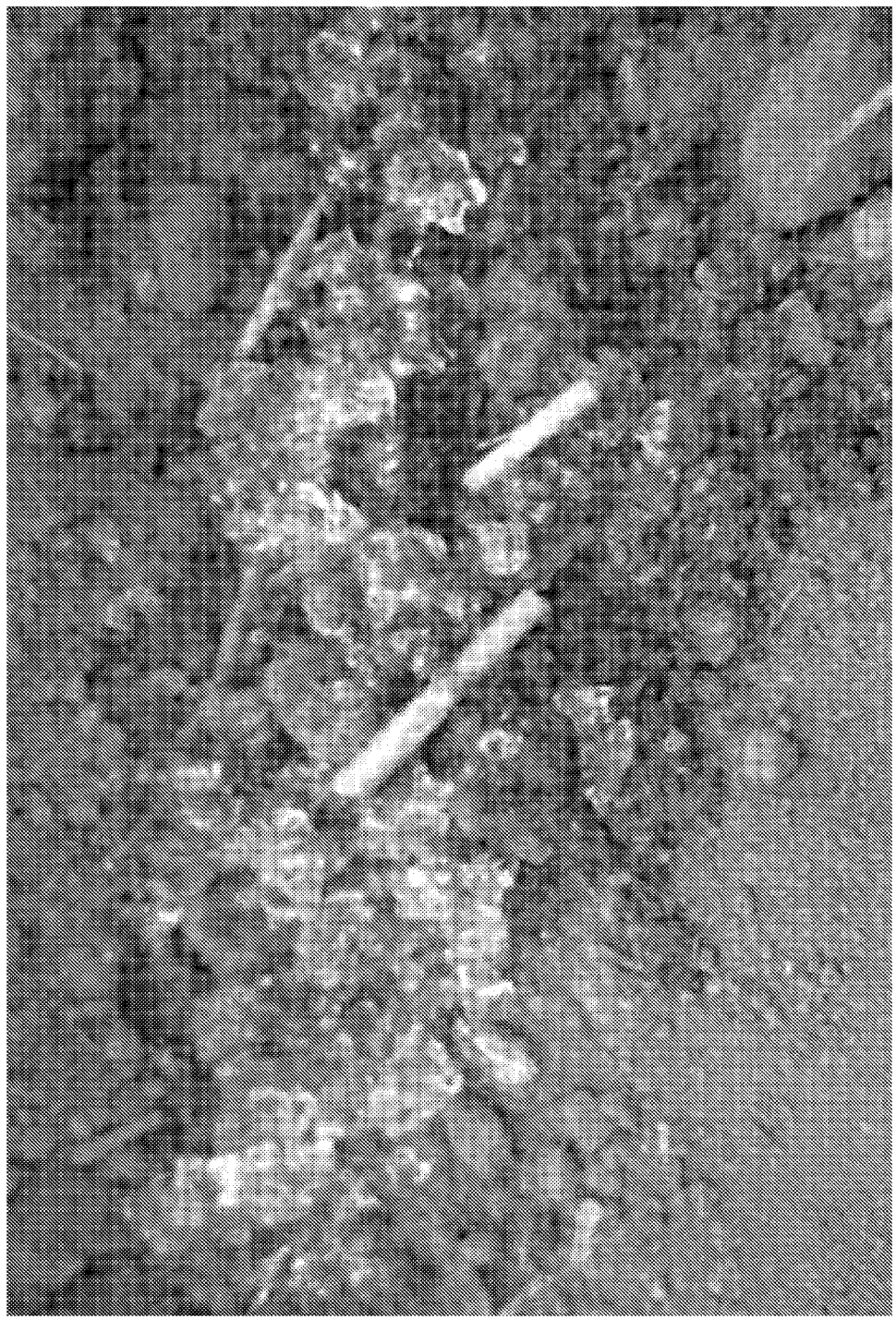
FIG. 21 shows the details of micro-nodes that were planted into soil using a subsoil shank.
Figure 22:
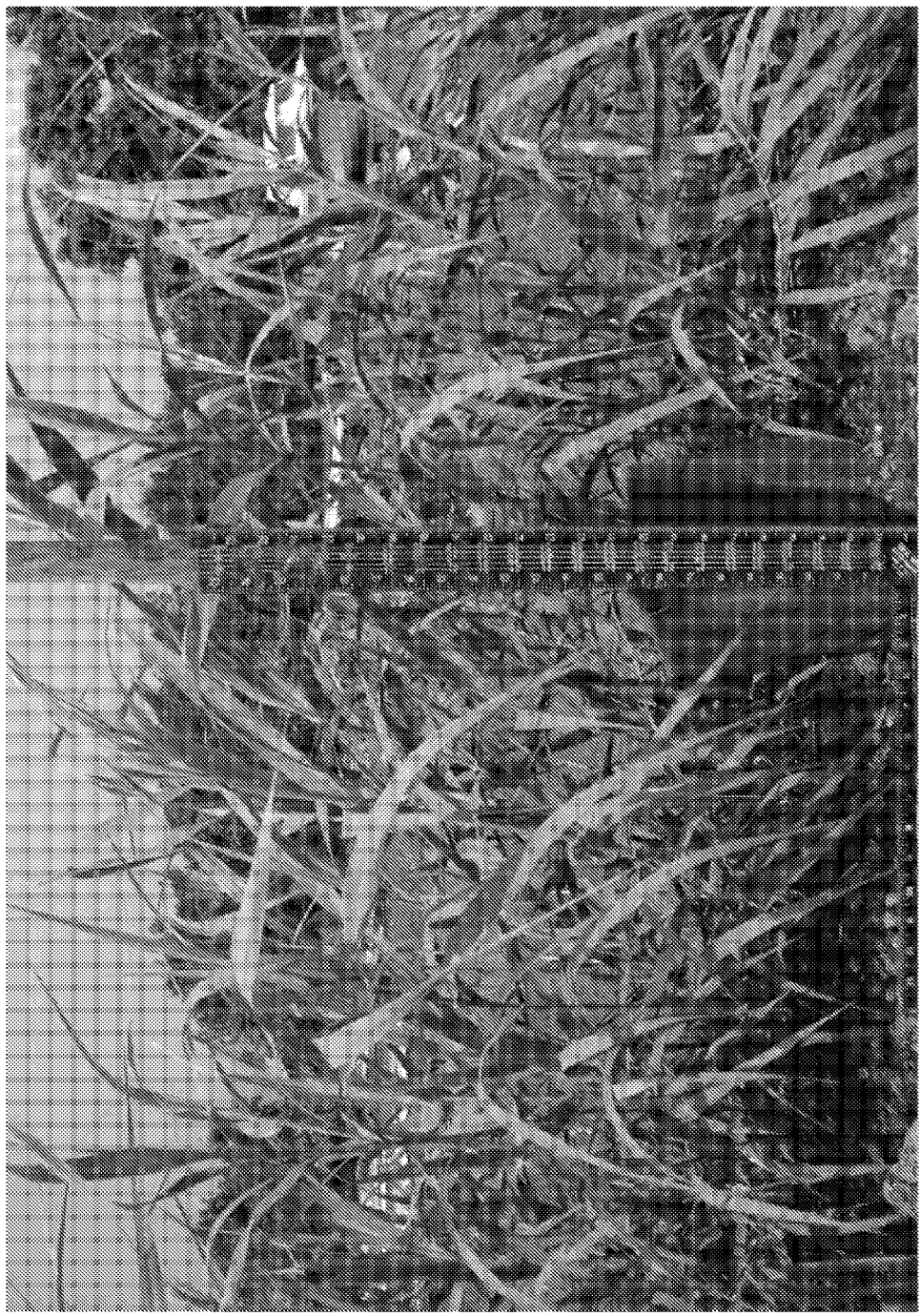
FIG. 22 shows Machias plants at about 5 months.
Figure 23:
FIG. 23 shows Machias plants at about 7 months.
Figure 24:
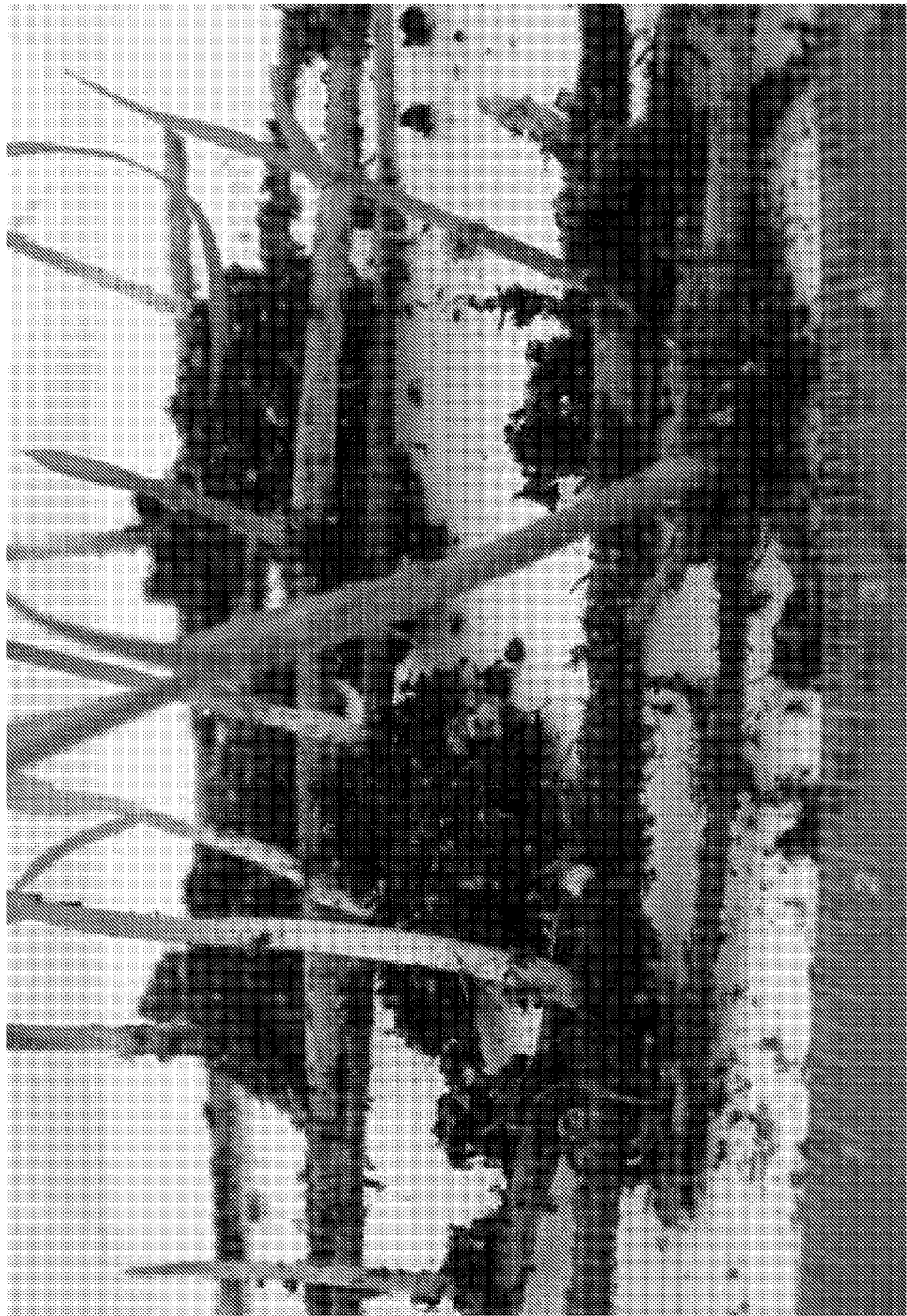
FIG. 24 shows stems (or ramets) removed from media showing root and shoot development.
Figure 25:
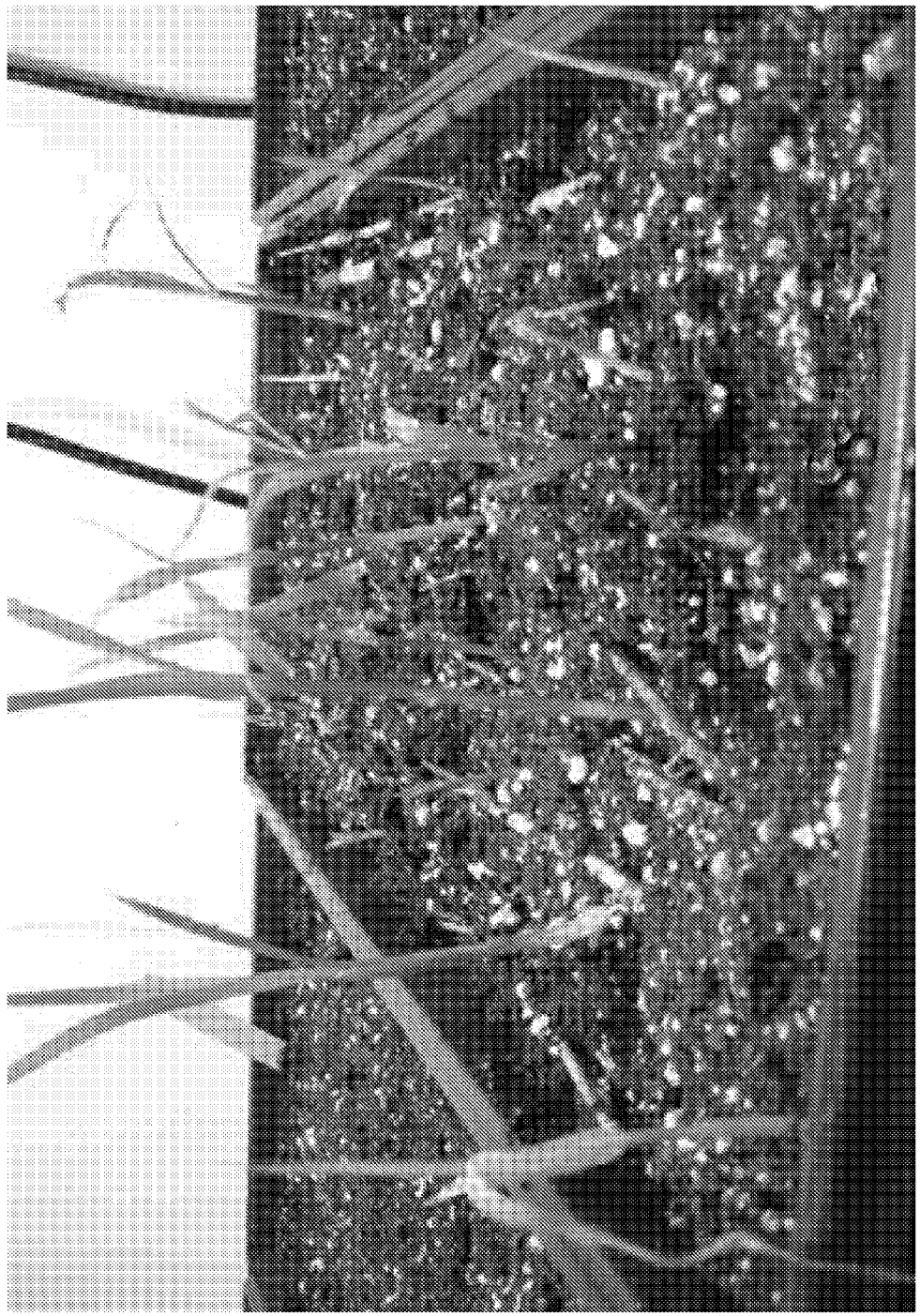
FIG. 25 shows immature stem (ramet) recruitment after 16 days from intact ramets.

As one example of such a method, the treated immature stems may be harvested by merely trimming the upper portions of the immature stem, and retaining the lower portions, such as the lower one or two or three or four nodes. The upper portions (i.e., the "seed stems") may then be planted in soil (sectioned or un-sectioned), if desired. In certain embodiments, the seed stems may be harvested or trimmed prior to the formation of pseudorhizomes. A "pseudorhizome" refers to a soft fleshy covered rhizome that has not yet developed the epidermis, or hard protective scale, of a mature rhizome. Generally, a pseudorhizome is between about 2 to 6 centimeters in diameter (see FIG. 10).

The lower portions of the trimmed stems may then be re-grown into immature stems, as described herein (e.g., stems about 10-25 inches tall and having about 4-10 nodes), and thereby serve as a mother plant. Similar to above, this step may take about 6-15 days (including all integers in between), about 1-8 weeks, about 2-6 weeks, about 3-4 weeks, including about 1, 2, 3, 4, 5, 6, 7, or 8 weeks. These re-grown immature stems may then be treated with a growth-enhancing composition (see step (d) above), allowed to grow for a selected time period (e.g., about 3-21 days), and then harvested again according to step (b) above, such as by trimming or removing the upper sections of the immature stems to obtain another batch of seed stems. The harvested seed stems may then be planted, and the lower portions of the mother plant re-grown into immature stems. As above, the steps of this method may be repeated as desired (see step (d) above), mainly to maintain a stock of seed stems, and to rapidly increase or amplify plant stock. In certain embodiments, the seed stocks may be harvested on a 4-10 week interval. At any point, certain of the treated immature stems may be either planted directly into the soil (sectioned or un-sectioned), or stored for later use or shipping or both.

As another example, the treated immature stems may be harvested by cutting the stems from step (a) into micro-segments, or micro-nodes (e.g., about ½ to about 1½ inches to about 2 inches or more in length and having at least one or two nodes). These micro-nodes may then be placed in a propagation bed or other apparatus, optionally treated or incubated with plant hormones (e.g., a growth-enhancing composition of the invention), and grown into immature stems (see step (c) above), as described herein (e.g., stems about 10-25 inches tall and having about 4-12 nodes). This step may take about 6-15 days (including all integers in between), about 1-8 weeks, about 2-6 weeks, about 3-4 weeks, including about 1, 2, 3, 4, 5, 6, 7, or 8 weeks. When ready, these immature stems may then be treated with a growth-enhancing composition (see step (d)), such as by spraying until runoff, allowed to grow for a selected time period (e.g., about 3-21 days), and then harvested again according to step (b). This process may be repeated as desired.

Using the methods provided herein, the treated immature stems typically elicit root and shoot formation about 3 days after planting in soil, if not before. Also, the planted stems typically grow to fully mature size in about 12 to 16 months, at which time they are ready for harvest. This rapid growth to maturity reduces the typical propagation cycle of grass plants (e.g., sterile grass plants) by about 12 weeks. Also, as noted herein, these plants achieve robust growth at minimal cost, and maintain the full genetic complement of the parent plants with no somaclonal variation, making them ideal for applications that require clonal uniformity.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for propagating a sterile grass plant, comprising:
   (a) treating an immature stem of a sterile grass plant or a segment thereof with a composition comprising: an auxin at 1 ppm to 10,000 ppm, a cytokinin at 1 ppm to 10,000 ppm, and polyaspartic acid at 1 ppm to 250,000 ppm, wherein the immature stem is 1 to 8 weeks old;
   (b) harvesting the stem treated in step (a); and
   (c) planting the stem harvested in step (b).

2. The method of claim 1, wherein step (a) is performed in situ.

3. The method of claim 2, wherein the immature stem is about 10-25 inches in height and has 4 to 10 nodes.

4. The method of claim 2, wherein the immature stem is 3 to 6 weeks old.

5. The method of claim 1, wherein step (b) is performed 3 to 20 days after step (a) is performed.

6. The method of claim 1, wherein step (b) is performed 12 to 16 days after step (a) is performed.

7. The method of claim 1, wherein the sterile grass plant is an *Arundo donax* plant, or a cultivar thereof.

8. The method of claim 1, wherein the sterile grass plant belongs to the family Poaceae.

9. The method of claim 1, wherein the sterile grass plant is an *Arundo gigantium, Geranium sagitatum, Miscanthus x giganteus, Saccharum officianarum* or other *Saccharum* spp., *Pennisetum purpereum* plant, or a cultivar thereof.

10. The method of claim 1, further comprising a seaweed concentrate at 1 ppm to 500,000 ppm.

11. The method of claim 1, further comprising a seaweed concentrate at 100 ppm to 1000 ppm.

12. The method of claim 10, wherein the seaweed concentrate is an extract from *Ascophyllum nodosum*.

13. The method of claim 1, further comprising a surfactant at 1 ppm to 250 ppm.

14. The method of claim 13, wherein the surfactant is Tween 20.

15. The method of claim 1, wherein the auxin is indole butyric acid (IBA), indole-3-acetic acid (IAA), naphthalene acetic acid (NAA), 4-chlorindole-3-acetic acid (4-Cl-IAA), 2-phenylacetic acid (PAA), 2,4-dichlorophenoxyacetic acid, 2-methoxy-3,6-dichlorobenzoic acid, 4-amino-3,5,6-tricholoropicolinic acid, or a mixture thereof.

16. The method of claim 1, wherein the cytokinin is benzylaminopurine (BA), kinetin, zeatin (Z), dihydrozeatin (DHZ) and isopentenyladenosine (IPA), ortho-topolin (oT), meta-topolin (mT), ortho-methoxytopolin (MeoT), meta-methoxytopolin (MemT), benzladenine (BA), or a mixture thereof.

17. The method of claim 1, wherein the polyaspartic acid is copoly-[(3-carboxypropionamide)(2-(carboxymethyl)acetamide)].

18. The method of claim 1, wherein the auxin is at 100 ppm to 1000 ppm.

19. The method of claim 1, wherein the cytokinin is at 100 ppm to 1000 ppm.

20. The method of claim 1, wherein the polyaspartic acid is at 500 ppm to 5000 ppm.

21. A composition for treating a grass plant in situ, comprising: an auxin at 100 ppm to 1,000 ppm, a cytokinin at 100 ppm to 1,000 ppm, and polyaspartic acid at 500 ppm to 5,000 ppm.

22. A method for producing seed stems, comprising:
(a) treating an immature stem of a sterile grass plant or a segment thereof with a composition that comprises an auxin at 1 ppm to 10,000 ppm, a cytokinin at 1 ppm to 10,000 ppm, and polyaspartic acid at 1 ppm to 250,000 ppm, wherein the immature stem is 1 to 8 weeks old;
(b) harvesting a portion of the stem treated in step (a) to produce a seed stem;
(c) growing the remaining portion of the stem of step (b) into an immature stem; and
(d) repeating steps (a) and (b) at least once, thereby producing seed stems.

23. The method of claim 22, wherein step (a) is performed in situ.

24. The method of claim 22, wherein the immature stem is 10-25 inches in height and has 4 to 10 nodes.

25. The method of claim 22, wherein the immature stem is 3 to 6 weeks old.

26. The method of claim 22, wherein step (b) is performed 3 to 20 days after step (a) is performed.

27. The method of claim 22, wherein step (b) is performed 14 days after step (a) is performed.

28. The method of claim 22, wherein step (b) is performed prior to pseudorhizome formation.

29. The method of claim 22, wherein step (d) is initiated 1-8 weeks after step (c) is performed.

30. The method of claim 22, wherein step (d) is initiated 3-6 weeks after step (c) is performed.

31. The method of claim 22, wherein the sterile grass plant is an *Arundo donax* plant.

32. The method of claim 22, wherein the sterile grass plant belongs to the family Poaceae.

33. The method of claim 22, wherein the sterile grass plant is an *Arundo gigantium, Geranium sagitatum, Miscanthus x giganteus, Saccharum officianarum* or other *Saccharum* spp., *Pennisetum purpereum* plant, or a cultivar thereof.

34. The method of claim 22, wherein the composition comprises the auxin at 100 ppm to 1,000 ppm, the cytokinin at 100 ppm to 1,000 ppm, and polyaspartic acis at 500 ppm to 5,000 ppm.

* * * * *